(12) United States Patent
Van Niekerk

(10) Patent No.: US 12,383,708 B2
(45) Date of Patent: Aug. 12, 2025

(54) MEDICAL DEVICE

(71) Applicant: STRATOS MEDICAL LIMITED, Galway (IE)

(72) Inventor: Henry Walter Van Niekerk, Hilton (CA)

(73) Assignee: STRATOS MEDICAL LIMITED, Galway (IE)

( * ) Notice: Subject to any disclaimer, the term of this patent is extended or adjusted under 35 U.S.C. 154(b) by 462 days.

(21) Appl. No.: 17/758,903

(22) PCT Filed: Jan. 14, 2021

(86) PCT No.: PCT/IB2021/050244
§ 371 (c)(1),
(2) Date: Jul. 15, 2022

(87) PCT Pub. No.: WO2021/144724
PCT Pub. Date: Jul. 22, 2021

(65) Prior Publication Data
US 2023/0050024 A1    Feb. 16, 2023

(30) Foreign Application Priority Data
Jan. 16, 2020  (ZA) .................. 2020/00295

(51) Int. Cl.
*A61M 25/06*   (2006.01)
*A61M 39/02*   (2006.01)

(52) U.S. Cl.
CPC ............ *A61M 25/06* (2013.01); *A61M 39/02* (2013.01)

(58) Field of Classification Search
CPC .. A61M 2025/0025; A61M 2025/0024; A61M 25/0074; A61M 25/0662; A61M 2025/0681
See application file for complete search history.

(56) References Cited

U.S. PATENT DOCUMENTS

| 4,368,738 A | 1/1983 | Teresteegen et al. |
| 4,552,554 A * | 11/1985 | Gould ................... A61M 25/01 604/164.13 |

(Continued)

FOREIGN PATENT DOCUMENTS

| WO | 9533509 A1 | 12/1995 |
| WO | 2010045702 A1 | 4/2010 |
| WO | 2011133395 A1 | 10/2011 |

OTHER PUBLICATIONS

European Examination Report prepared for European Application No. EP21741581, completed Aug. 5, 2024.

(Continued)

*Primary Examiner* — Nilay J Shah
(74) *Attorney, Agent, or Firm* — Pierce Atwood LLP

(57) ABSTRACT

This invention relates to a medical device. The device includes an elongate cannula which is insertable into a blood vessel and which is resiliently biased towards a closed condition in which it inhibits fluid flow through the cannula. The cannula is displaceable away from its closed position by the introduction of a displacement arrangement such as a device or instrument or a pressurised fluid and reverts to its closed condition when the displacement arrangement is removed from the cannula to inhibit the flow of blood therethrough. The invention further relates to a needle for use with the medical device, to a kit and to a method of accessing a blood vessel. In addition, it relates to a method of closing an incision in a blood vessel and to a closure member for use in the method.

15 Claims, 25 Drawing Sheets

(56) References Cited

U.S. PATENT DOCUMENTS

| | | | |
|---|---|---|---|
| 4,795,426 A * | 1/1989 | Jones | A61B 17/3421 |
| | | | 604/164.11 |
| 5,112,312 A * | 5/1992 | Luther | A61M 25/0637 |
| | | | 604/177 |
| 5,522,807 A * | 6/1996 | Luther | A61M 25/0068 |
| | | | 604/523 |
| 5,752,970 A | 5/1998 | Yoon | |
| 5,916,194 A * | 6/1999 | Jacobsen | A61M 25/0105 |
| | | | 604/524 |
| 6,962,575 B2 | 11/2005 | Tal | |
| 7,261,705 B2 | 8/2007 | Edoga et al. | |
| 7,811,264 B2 | 10/2010 | Claude et al. | |
| 9,072,880 B2 | 7/2015 | Phillips et al. | |
| 9,295,773 B2 | 3/2016 | Prosl et al. | |
| 9,937,296 B2 | 4/2018 | Peh et al. | |
| 10,835,663 B2 | 11/2020 | Peh et al. | |
| 2003/0158514 A1 | 8/2003 | Tal | |
| 2004/0147877 A1 | 7/2004 | Heuser | |
| 2004/0254541 A1 | 12/2004 | Wong et al. | |
| 2005/0043703 A1 | 2/2005 | Nordgren | |
| 2008/0312577 A1 | 12/2008 | Drasler et al. | |
| 2014/0100603 A1 | 4/2014 | Aravot et al. | |
| 2014/0364766 A1 | 12/2014 | Devgon et al. | |
| 2014/0378893 A1 | 12/2014 | Tsyrulnyko | |
| 2015/0141925 A1 | 5/2015 | Bandera | |
| 2017/0021087 A1 | 1/2017 | Prost et al. | |
| 2017/0043086 A1 | 2/2017 | Popa-Simil | |
| 2018/0000512 A1 | 1/2018 | Dickinson et al. | |
| 2018/0221593 A1 | 8/2018 | Peh et al. | |
| 2021/0077705 A1 | 3/2021 | Claude et al. | |

OTHER PUBLICATIONS

PCT International Preliminary Report on Patentability prepared for PCT Application No. PCT/IB2021/050244, completed Nov. 10, 2021.

European Search Report prepared for European Application No. EP21741581, completed Nov. 15, 2023.

PCT Search Report and Written Opinion prepared for PCT Application No. PCT/IB2021/050244, completed Apr. 30, 2021.

* cited by examiner

MEDICAL DEVICE

CROSS-REFERENCE TO RELATED APPLICATIONS

This application is a national stage entry under 35 U.S.C. § 371(b) of PCT International Application No. PCT/IB2021/050244, filed Jan. 14, 2021, which claims the benefit of South African Patent Application Serial No. 2020/00295, filed on Jan. 16, 2020, the entire disclosures of both of which are incorporated herein by reference.

This invention relates to a medical device. It further relates to a needle for use with the medical device, to a kit and to a method of accessing a blood vessel. It further relates to a method of closing an incision in a blood vessel and to a closure member for use in the method.

For various medical reasons access may be required to various blood vessels in a patient's body.

One such reason is for dialysis, where patients with end-stage renal disease (ESRD) need chronic dialysis or a kidney transplant to replace the function of their kidneys. Both haemodialysis and peritoneal dialysis are options. Dialysis needs to happen on a regular, life-long basis. Patients on haemodialysis will typically have dialysis three times a week, for three to five hours at a time.

Haemodialysis (HD) consists of circulating a vast amount of blood through a dialysis machine containing filters to effect particle and water exchange. A crucial element of successful HD is access to a high volume of blood that can feed the pump, and the ability to pump the 'cleaned' or treated blood back into the body.

Two options exist to 'access' the bloodstream, namely:
e HD-line
AV-fistula

When using an HD-line, a large-calibre catheter with 2 channels is placed percutaneously into a large central vein (Central Venous Catheter, or CVC-haemodialysis). This works well in the short term, but is problematic for longer periods because irritation caused by the catheter leads to scar formation in the blood vessel, eventually causing structuring (narrowing) and occlusion. There is also a high risk of catheter infection and venous thrombosis.

Currently, the only long-term HD access option is creating an arteriovenous fistula, 'AV-fistula'. This is usually done by a small surgical procedure where an adequately sized vein in the arm is connected to an artery. Connecting the artery directly to the vein results in a substantial increase in blood flow in the vein typically of the order of a forty-fold increase in the volume. In addition, the pressure in the vein is typically about four times higher than before the connection to the artery. Over the subsequent six weeks, by virtue of the increase in volume and pressure, the vein (now called a 'fistula'), undergoes a process of maturation, with thickening of the wall, as well as dilatation (widening) of the vessel.

Six weeks later the fistula can be 'needled', which means that two thick steel needles are used to puncture the vein and gain access to the bloodstream whereby the vein can be connected in flow communication respectively with an inlet and an outlet of the dialysis machine.

When no big veins are available in the arms to create a fistula, surgeons use a prosthetic graft to make a connection between an artery and vein in the arm. This graft is then punctured during dialysis.

A fistula can typically be used for between one to five years. Unfortunately, with every needling of the fistula, i.e. in preparation for a dialysis treatment, there is some damage to the wall. Over time this leads to weakening and thinning of the wall, as well as areas of narrowing due to scar formation. Invariably the fistula thromboses (clots up), and if the problematic area cannot be rectified by stretching it with a balloon or replacing it with healthy vein or a section of prosthesis, the fistula can no longer be used.

The failure of fistulas is an enormous problem in the management of ESRD patients. Without dialysis these patients die within one to four weeks. Vast amounts of time, energy and resources are used to keep AV-fistulae open, initially when creating the fistula and then subsequently when there is stenosis (narrowing) or thrombosis (clotting). A limited number of fistulas can be attempted on any one patient, available options are 'used up' when fistulas fail. Lack of dialysis access remains one of the leading causes of death in ESRD patients.

Further, most dialysis takes place in dedicated dialysis units such as in hospitals and medical clinics. Patient's usually dialyse three times a week for up to 5 hours at a time. Naturally, this is not only inconvenient, but it is also extremely disruptive, especially for people who are working.

In addition, the Inventor is aware of the fact that, when conducting other medical procedures, several instruments may need to be introduced into and removed from a blood vessel. For example, in many coronary procedures access to the heart is gained via the femoral artery. This usually involves placing an end portion of a guide wire into the femoral artery after ultrasound-guided puncture of the femoral artery with a thin needle. A sheath of substantially larger diameter, typically 2 mm to 4 mm is then fed over the guide wire and pushed into the artery using a simple dilator. This results in a relatively large circular hole being formed in the wall of the artery.

The procedure on the heart is then performed through the femoral access site. This, for example, could include the insertion and removal of numerous devices and/or catheters such as a balloon catheter and then a stent being manoeuvre into a diseased coronary artery. High doses of anticoagulants are given during the procedure. Some of the anticoagulants work out within a few hours and others may be administered continuously for months.

Typically, the sheath will be removed 2-3 hours after the procedure when the effect of a primary anticoagulant such as "Aggrastat" has worn off.

As a consequence of the relatively large hole which is formed in the wall of the femoral artery, in combination with systemic anticoagulation, bleeding from the puncture site is common. This ranges from small hematomas which can result in significant patient discomfort, false aneurysm formation which may require surgical intervention to potentially life-threatening retro-peritoneal bleeding.

In an attempt to address this issue use is often made of closure devices which are installed at the site of the incision. This adds cost and complexity to the procedure.

It is an object of this invention to provide means that the Inventor believes will ameliorate at least some of these problems.

According to one aspect of the invention, there is provided a medical device which includes an elongate cannula having a distal end which is insertable into a blood vessel, a proximal end and a closure arrangement which is resiliently biased towards a closed condition in which it inhibits fluid flow through the cannula, at least from the distal end to the proximal end, and which is displaceable against the bias away from its closed condition by the introduction of a displacement arrangement into the cannula and reverts to its closed condition when the displacement arrangement is removed from the cannula.

The Inventor believes that the medical device will be suitable for use in many different applications. One such application is during haemodialysis. In this application, the distal end of the cannula is inserted into a blood vessel such as a large vein, e.g. the internal jugular vein or a fistula formed in the manner described above. By virtue of the fact that the closure arrangement is biased towards and normally in a closed condition, no or little blood will leak through the cannula. When a patient is to undergo dialysis, a tubular needle is inserted into the cannula and urges the closure arrangement away from its closed condition to permit a distal end of the needle to be in flow communication with the interior of the blood vessel, a proximal end of the needle being connected in flow communication with a dialysis machine.

Once the dialysis treatment has been completed, the needle is removed from the cannula which then reverts to its closed condition preventing excessive bleeding from the blood vessel.

At least a portion of the cannula may be formed of a resiliently deformable material which has a rest condition, towards which it is resiliently biased, in which it effectively closes off a lumen extending through the cannula and forms the closure arrangement of the cannula.

The resiliently deformable material may be displaceable away from its rest position by the insertion of a device or instrument through the cannula lumen towards the distal end. It will be appreciated that when the device or instrument is removed from the cannula, the cannula will revert to its closed condition thereby minimising or preventing blood flow through the cannula. The resiliently deformable material may also be displaceable away from its rest position by the introduction of a pressurised fluid into the cannula, e.g., to flush the cannula. It will be appreciated that when introducing a fluid into the cannula the displacement of the deformable material away from its rest position will just be sufficient to permit the passage of the fluid therethrough.

The portion of the cannula which is formed of the resiliently deformable material may be a distal end portion which extends longitudinally inwardly from the distal end of the cannula for at least part of the length of the cannula.

The resiliently deformable material may be a flexible polymeric material such as silicone.

When the instrument or device is withdrawn from the cannula, the resiliently deformable portion reverts to its rest condition to effectively close off the lumen. The cannula can be left in position with its distal end in the blood vessel permitting its use for multiple dialysis treatments. In the case of a fistula, this reduces the frequency with which the fistula must be needled thereby greatly extending the period of time that the fistula can be used. A further advantage is that this also reduces the frequency with which a patient must endure the discomfort associated with the needling of the fistula. In addition, it makes subsequent access to the blood stream far easier, thereby making home dialysis more accessible.

The distal end portion of the cannula may have an arcuate or crescent shape in transverse cross-section when in its rest condition. When introducing the cannula into a fistula, use would be made of a fistula puncture needle or cutting tipped needle. When a fistula needle penetrates the fistula a sharpened leading portion of the needle forms an arcuate incision in the wall of the fistula which incision has an outer or convex side and an inner or concave side. The portion of the fistula wall adjacent the inner or concave side of the incision effectively forms a semi-circular flap or curtain. The semi-circular margin of the curtain is effectively pulled into the elastic wall of the fistula as the blunt ridges of the following half of the bevelled placement needle stretch the hole open. When the cannula of the present invention is inserted through the incision in the fistula wall the arcuate cross-section of the cannula when in its rest condition corresponds in shape to the shape of the incision. This results in minimal displacement of the wall of the fistula forming the curtain which minimises the risk of bleeding from the point of entry of the cannula into the fistula. Naturally, this approach is not limited to a fistula and/or haemodialysis can be followed when accessing other blood vessels for various different reasons.

The medical device may include a head to which the distal end portion of the cannula is connected and from which it protrudes. The head may be formed of a rigid or semi-rigid material and is provided with gripping formations to facilitate manipulation of the device. The head may be coated with a soft material to improve patient comfort.

The cannula may include a proximal end portion which protrudes from the head in a direction opposite to the direction in which the distal end portion protrudes and which is connected in flow communication with the distal end portion. The proximal end portion may be rigid.

The medical device may include a cap which is dismountably mountable to cover an open end of the proximal end portion remote from the distal end portion. The cap may be coated with a soft material to enhance patient comfort. The cap and the head or the proximal end portion may have complementary locking formations, e.g. in the form of screw threads, whereby the cap is releasably lockable in position.

A stylet may be connected to and protrude from the cap, the stylet being received at least in the proximal end portion of the cannula when the cap is mounted thereto. As mentioned above, once a dialysis treatment has been completed the needle which connects the blood vessel to the dialysis machine is removed from the cannula. The distal end portion of the cannula will revert to its closed condition. The cannula may then be flushed by injecting a heparin-saline solution under pressure thereby overcoming the closing-force of the distal end portion of the cannula. The cap is then mounted on the head with the stylet positioned in the proximal end portion which obliterates space within the cannula lumen which reduces the volume of blood, if any, contained in the cannula between dialysis treatments thereby pre-empting thrombus formation that would otherwise predispose to thromboembolisation.

A transverse opening may be provided in a side or wall of the cannula at a position closely spaced from the distal end thereof.

At least a distal end portion of the cannula may be treated with chemicals to inhibit blood clotting and/or infection. The end portion of the cannula may be coated and/or impregnated with at least one of heparin, silver and an antibiotic.

At least a distal end portion of the cannula may be formed of a bioresorbable material, i.e. a material that can be broken down and absorbed by the body. This permits the distal end portion to be left in position even after access to the blood vessel is no longer required. The remaining distal end portion then effectively forms a closure member or plug in the incision site until the blood vessel has healed.

The medical device may include a placement needle on which the cannula is mounted and relative to which the cannula is longitudinally displaceable to facilitate placement of the cannula.

The medical device may include a guide wire engagement arrangement configured to engage with a guide wire to facilitate correct placement of the placement needle and hence of the cannula. The guide wire engagement arrangement may include a guide wire tube which extends along a bore in the placement needle and which is dimensioned to receive a guide wire slidably therein.

According to another aspect of the invention, there is provided a needle for use with a medical device of the type described above, which needle has a distal end and a proximal end, the distal end being shaped and dimensioned to be inserted through the cannula of the medical device into flow communication with a blood vessel into which the distal end of the cannula has been inserted.

The needle may have a blunt or rounded tip such that it can displace the closure arrangement away from its closed condition without causing any damage to the cannula or the blood vessel.

The needle may include locking means configured to cooperate with complementary locking means on the medical device in order to lock the needle releasably to the medical device once the needle has been inserted through the cannula into the blood vessel. The locking means may include complementary male and female connectors provided on the cannula and on the needle.

The needle may include a transverse opening positioned adjacent to the distal end of the needle.

It will be appreciated that the specific configuration of the needle may depend upon the intended application.

In one embodiment of the invention, the needle may be a dialysis needle, the proximal end of the dialysis needle being connectable in flow communication with a dialysis machine.

In another embodiment of the invention, the needle may be a blunt-tipped atraumatic needle which is connected or connectable to a "Vacutainer" or other venepuncture system.

In yet another embodiment of the invention, the needle may be configured to introduce fluid such as from a syringe or a drip-IV-system into the blood vessel.

According to a further aspect of the invention, there is provided a kit which includes a medical device of the type described above and/or a needle of the type described above contained in hermetically sealed sterile packaging.

According to yet another aspect of the invention, there is provided a kit which includes at least one medical device of the type described above and at least one complementary needle which is insertable through the cannula into flow communication with the blood vessel.

The needle may have a length which is selected such that when the needle is inserted into the cannula of the medical device the distal end of the needle protrudes beyond the distal end of the cannula.

A transverse opening may be provided in a side or wall of the cannula at a position closely spaced from the distal end thereof and a complementary transverse opening may be positioned adjacent to the distal end of the needle such that when the needle is inserted into the cannula the transverse openings in the cannula and the needle are in register thereby permitting fluid flow therethrough. Hence, if for some reason, the distal end of the needle is obstructed, e.g., by being in contact with the wall of the blood vessel opposite the incision, the interior of the needle and the blood vessel are still connected in flow communication through the aligned transverse openings in the cannula and the needle.

The kit may include a cutting tipped needle for forming an incision in a blood vessel through which the cannula can be introduced into the blood vessel.

The cannula and cutting tipped needle may be provided with orientation means to ensure correct orientation of the cannula relative to the incision.

The kit may include a plurality of cannulae, each having different lengths and complementary dialysis or other needles. It may be preferable to provide a number, e.g. three, different lengths of cannulae (with corresponding longer or shorter placement, as well as dialysis needles), in order to custom-fit the device to fistulae that are located closer to the skin (more superficial), or deeper. Different colours may be used to easily tell the differing length cannulae apart, viz. short (blue), medium (pink) or long (green) devices.

The kit may include retaining means whereby the medical device can be retained in position on a patient. e.g. a soft, low-profile elastic band/strap to be worn around the arm containing the device when the patient is not in the dialysis unit, especially at night time while the patient is sleeping. This will prevent accidental dislodgement of the device. A tight, waterproof band may also be provided to patients who would like to swim with their device.

According to still another aspect of the invention there is provided a kit which includes a cutting tipped needle for forming an arcuate or crescent shaped incision in a blood vessel and an elongate cannula having a distal end which is insertable into a blood vessel and a proximal end, a distal end portion of the cannula having an arcuate or crescent shape in transverse cross-section which is complementary in shape to the incision formed by the cutting tipped needle to facilitate the insertion of the distal end of the cannula into the blood vessel through the incision.

According to a still further aspect of the invention, there is provided a method of accessing a blood vessel which method includes:
  inserting a needle with a cutting tip into the body of a patient to form an incision in a wall of the blood vessel; and
  introducing a distal end of the cannula of a medical device of the type described above through the incision into the blood vessel.

According to still yet another aspect of the invention there is provided a method of accessing a blood vessel which method includes:
  inserting a needle with a cutting tip into the body of a patient to form an arcuate or crescent shaped incision in a wall of the blood vessel; and
  providing an elongate cannula having a distal end which is insertable into a blood vessel and a proximal end, a distal end portion of the cannula having an arcuate or crescent shape in transverse cross-section which is complementary in shape to the incision formed by the cutting tipped needle; and
  inserting the distal end of the cannula through the incision into the blood vessel.

The method may include inserting a distal end of a dialysis needle through the cannula into the blood vessel and connecting a proximal end of the dialysis needle in flow communication with a dialysis machine. The dialysis needle can be connected to a dialysis machine either before or after inserting it into the cannula.

To ensure correct orientation of the cannula, both the cutting needle and the cannula may be provided with orientation means, e.g. in the form of visible and/or tactile markings.

The method may include replacing the cannula with a fresh cannula as required, e.g., when access is required to the blood vessel over an extended or ongoing period of time such as for dialysis where the cannula may be left in position for several dialysis sessions.

Replacing the cannula may include providing a replacement rod having a distal end and a proximal end, inserting the distal end of the replacement rod into the cannula which is already in position, displacing the cannula along the replacement rod towards the proximal end and removing the cannula from the replacement rod, displacing a fresh cannula, distal end first along the replacement rod until the distal end of the fresh cannula is positioned in the blood vessel and removing the replacement rod. It will be appreciated that the already installed cannula, i.e. the cannula to be removed will serve as a guide for the placement of the replacement rod which will then in turn serve as a guide for the placement of the fresh cannula.

The fresh cannula may be provided on a placement needle, the placement needle having a bore extending inwardly from a distal end thereof, the replacement rod having a proximal end portion which is dimensioned to be received in the bore in the placement needle, displacing the fresh cannula may then include positioning the placement needle on the replacement rod and sliding the fresh cannula longitudinally from the placement needle and along the placement rod. The replacement rod and the placement needle may be provided with complementary orientation formations to ensure correct alignment of the fresh cannula with the incision in the wall of the blood vessel.

According to a still further aspect of the invention, there is provided method of closing an incision or puncture in a blood vessel which includes the step of inserting a closure member of a bio-resorbable material into the incision to inhibit blood flow through the incision.

The closure member may be formed by an end portion of a cannula which is left in position in the incision. Hence, when access is no longer required to the blood vessel the cannula may be cut such that the distal end portion of the cannula remains in position in the incision to form the closure member and the remainder of the cannula is removed.

According to still yet a further aspect of the invention, there is provided a closure member for use in the above method, the closure member including a body of a bio-resorbable material which is shaped and dimensioned to be a snug fit in the incision in the blood vessel.

At least part of the body may be crescent shaped in transverse cross-section.

The invention will now be described, by way of example, with reference to the accompanying diagrammatic drawings.

DETAILED DESCRIPTION OF AN EXAMPLE EMBODIMENT

The following description of the invention is provided as an enabling teaching of the invention. Those skilled in the relevant art will recognise that many changes can be made to the embodiments described, while still attaining the beneficial results of the present invention. It will also be apparent that some of the desired benefits of the present invention can be attained by selecting some of the features of the present invention without utilising other features. Accordingly, those skilled in the art will recognise that modifications and adaptations to the present invention are possible and can even be desirable in certain circumstances, and are a part of the present invention. Thus, the following description is provided as illustrative of the principles of the present invention and not a limitation thereof.

Figure 3:
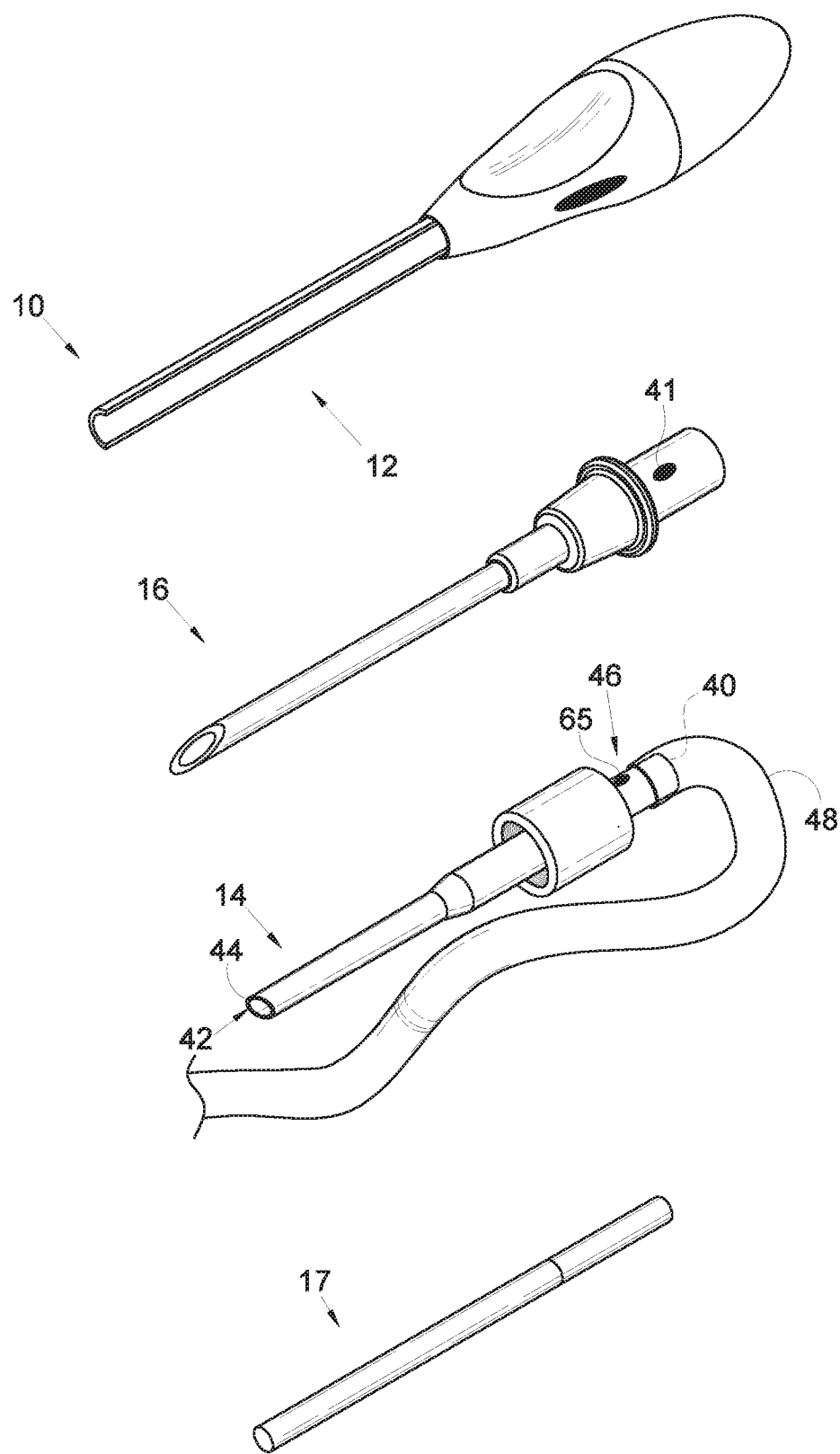
FIG. 3 shows part of a kit in accordance with the invention.

In FIG. 3 of the drawings, reference numeral 10 refers generally to a kit in accordance with the invention. The kit is intended for use in dialysis, however, the kit or parts thereof may find use in other applications.

Figure 24:
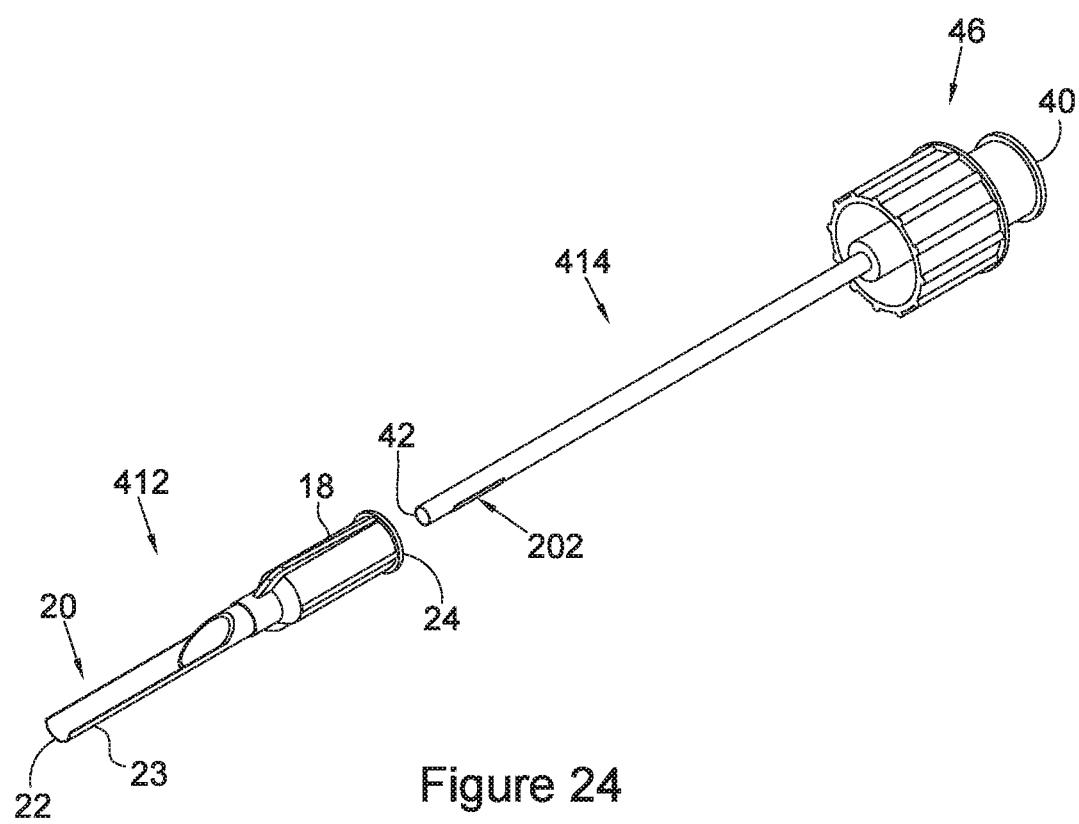
FIG. 24 shows a three-dimensional exploded view of another embodiment of a medical device and an associated needle in accordance with the invention.

The kit 10 includes a medical device in accordance with the invention, generally indicated by reference numeral 12, and a needle, generally indicated by reference numeral 14, for use with the device as described in more detail herebelow. Optionally, the kit 10 further includes a cutting tipped needle, generally indicated by reference numeral 16 and/or a needle, generally indicated by reference numeral 17, the purpose of which will be described in more detail below. It will be appreciated that the components of the kit may vary in form. Accordingly, FIG. 24 illustrates another embodiment of a medical device, generally indicated by reference numeral 412, and an associated needle, generally indicated by reference numeral 414, in accordance with the invention.

The kit 10 includes packaging (not shown) wherein the components of the kit are contained. The packaging is typically hermetically sealed and sterile such that the components of the kit are removed therefrom when intended to be used.

As can best be seen in FIGS. 4 to 6 and FIG. 24 of the drawings, the medical device 12, 412 includes a head 18 which is formed of a rigid or semi-rigid material and a cannula 20 which extends through the head 18. In the embodiment shown in FIGS. 4 to 6 of the drawings, the cannula 20 has a distal end 22 and a proximal end 24 which are positioned on opposite sides of the head 18. A lumen or passage 26 (FIG. 9) extends through the cannula 20 and opens out of the ends 22, 24.

Figure 9:
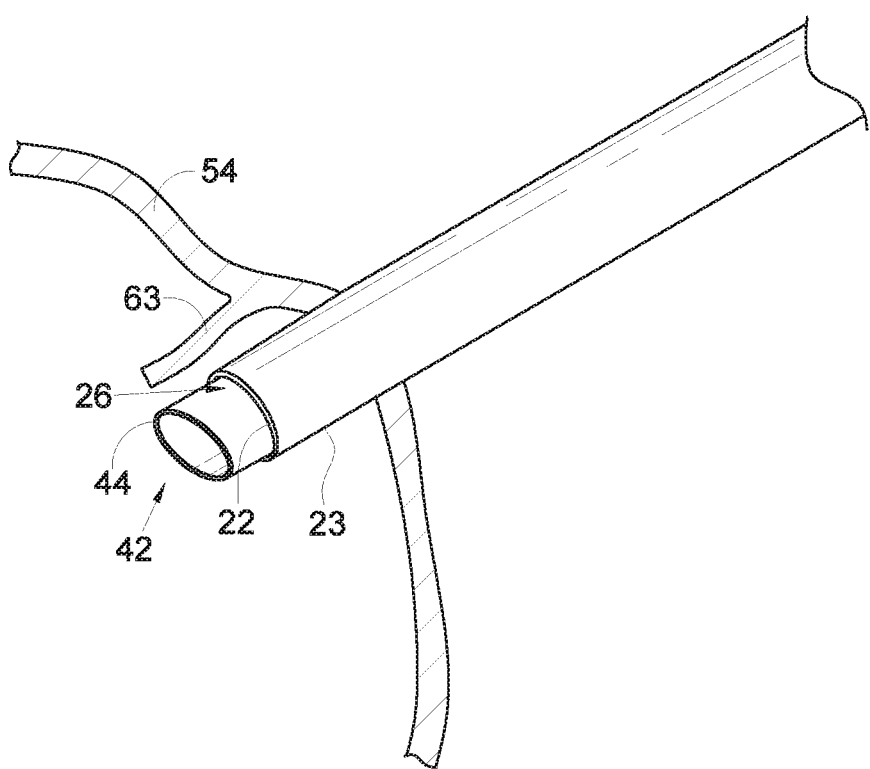
FIG. 9 shows a needle of the kit inserted into the cannula of the device.

A proximal end portion 25 of the cannula 20, i.e. the portion of the cannula 20 extending from the proximal end 24 into the head 18 is formed of a rigid tubular material which is circular in transverse cross-section. A distal end portion 23 of the cannula 20, i.e. the portion of the cannula extending longitudinally inwardly from the distal end 22 is formed of a resiliently deformable material, such as silicone, and is displaceable between a rest or closed condition (shown in FIGS. 4, 5 and 6 of the drawings) and an open condition (FIG. 9 of the drawings). The material of the distal end portion of the cannula has a memory and is biased towards its closed condition. In the closed condition of the end portion 23, it effectively closes off the lumen 26 and forms a closure arrangement to inhibit the flow of fluid through the cannula from the distal end 22 as described in more detail herebelow.

The head 18 includes opposed gripping formations 28 to facilitate manipulation of the device 12 as described in more detail herebelow. An orientation marking 30 is provided on the head 18 between the gripping formations 28.

Figure 4:
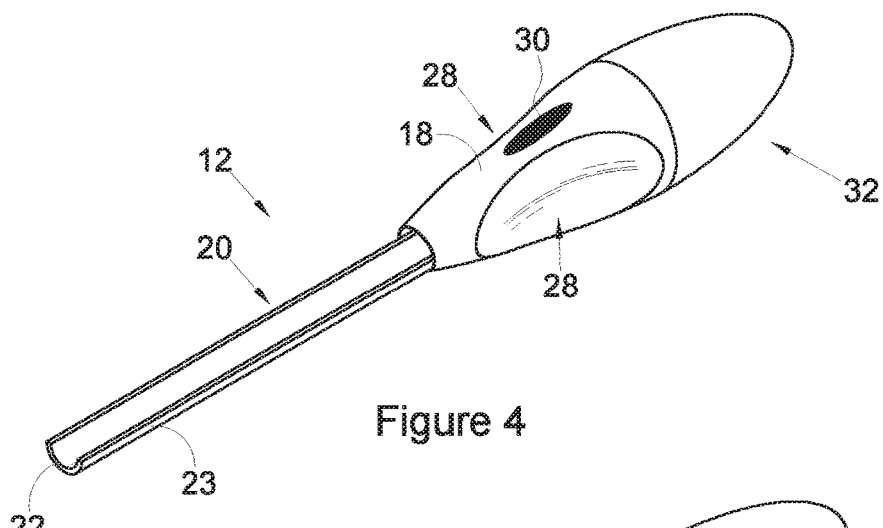
FIG. 4 shows a three-dimensional view of a medical device in accordance with the invention.
Figure 5:
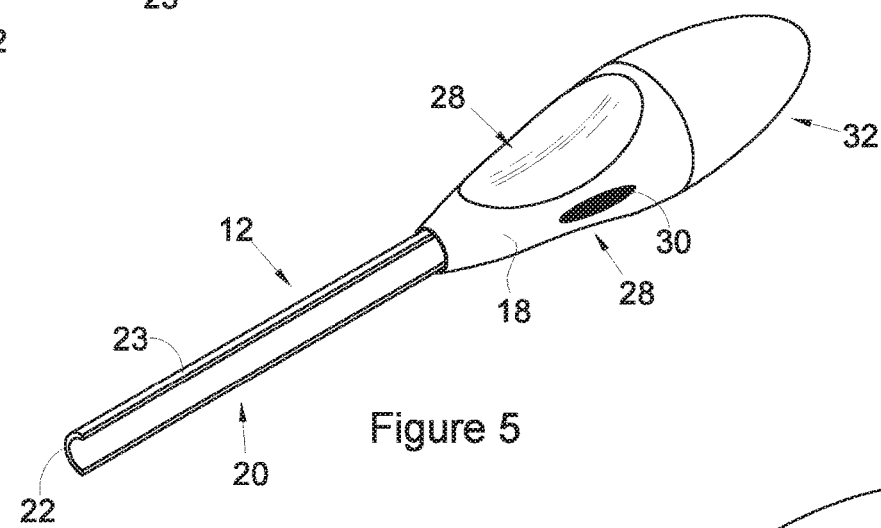
FIG. 5 shows a three-dimensional view of the device of FIG. 4 turned through 90°.
Figure 6:
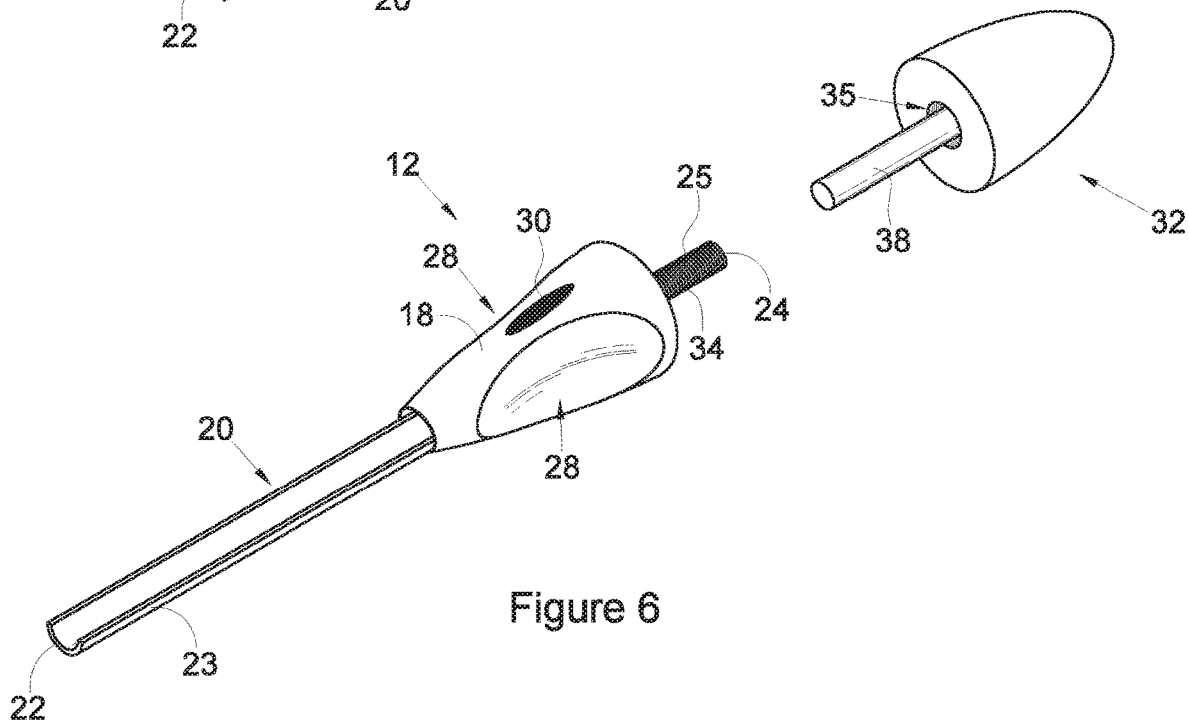
FIG. 6 shows a three-dimensional exploded view of the device of FIG. 4.

In the embodiment shown in FIG. 24 of the drawings, the distal end portion 23 of the cannula 20, is similar to the distal end portion 23 of the cannula shown in FIGS. 4 to 6 of the drawings. However, the proximal end of the cannula is positioned inside the head 18 and does not protrude therefrom.

The device 12,412 further includes a cap (not shown in FIG. 24), generally indicated by reference numeral 32. The cap 32 and cannula 20 have complementary locating formations whereby the cap 32 is releasably lockable in a closed position. In the embodiment shown, the locking formations are in the form of a male screw-thread 34 which is provided on the proximal end portion 25 of the cannula 20 and extends longitudinally inwardly from the proximal end 24 towards the head 18 and a complementary female screw-thread provided in a hole 35 in the cap 32. An elongate stylet 38 is connected to and protrudes from the cap 32. The stylet 38 is dimensioned such that when the cap 32 is screw-threadedly mounted on the cannula 20, the stylet is inserted into and extends longitudinally along the cannula 20 from the proximal end 24 for part of its length.

Figure 1:
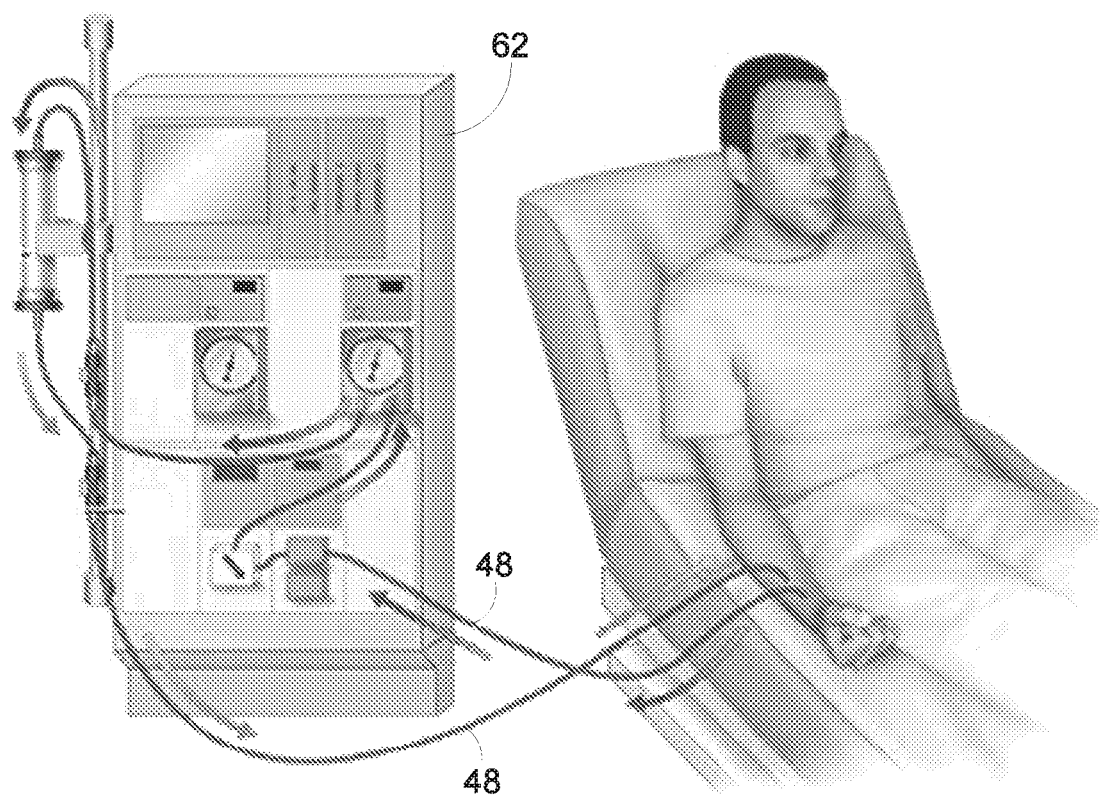
FIG. 1 shows diagrammatically a patient undergoing a dialysis treatment.

With reference to FIGS. 3 and 24 of the drawings, the needle 14,414 is a stainless steel dialysis needle having a proximal end 40 and a distal end 42. The needle is circular in transverse cross-section and has a rounded tip 44 at its distal end. An outer diameter of the needle 14 is selected such that it is snuggly and slidingly receivable through the lumen 26 in the device 12,412 as described in more detail herebelow. A connecting arrangement, generally indicated by reference numeral 46, is provided at the proximal end 40 of the needle 14,414 to permit the connection of the needle 14,414 to a dialysis machine 62 (FIG. 1) by way of an elongate flexible pipe 48. It will be appreciated that, instead of stainless steel, the needle 14,414 can be formed of any suitable material.

Figure 10:
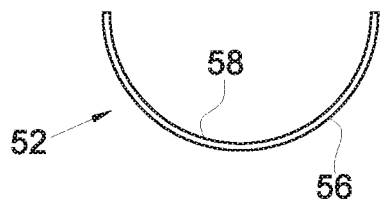
FIGS. 10 to 13 show sequentially the deformation of the wall of the fistula as the needle is inserted into the cannula and through the wall of the fistula.
Figure 17:
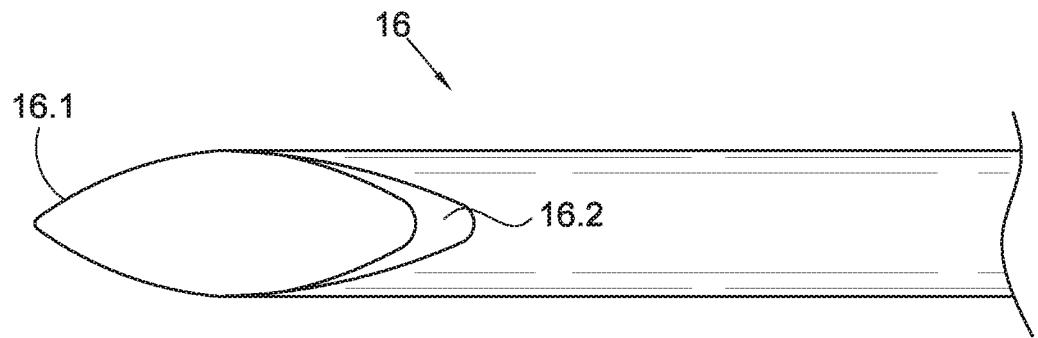
FIG. 17 shows, on an enlarged scale a top view of an end portion of the cutting needle.
Figure 18:
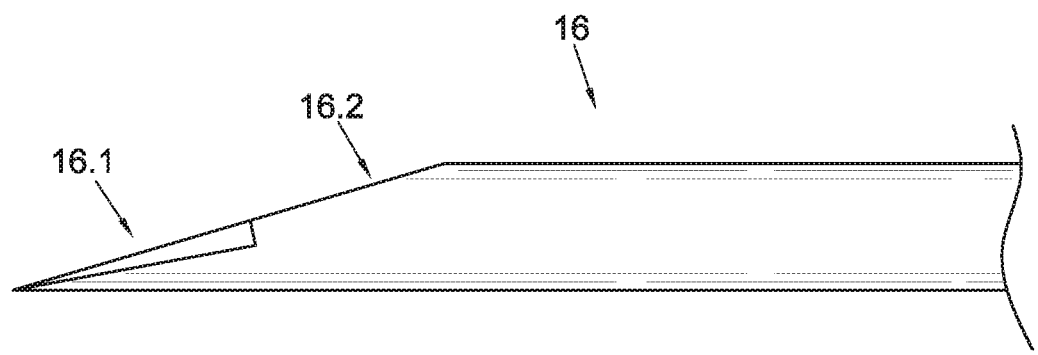
FIG. 18 shows a side view of the end portion of the cutting needle of FIG. 23.

The cutting-tip needle 16 is a conventional cutting-tip stainless steel needle which, in use, is used to penetrate a wall 54 of a fistula 50 and form an arcuate incision 52 (FIGS. 7 and 10) in the wall 54 of the fistula 50. As can be seen in FIGS. 17 and 18, the tip of the needle 16 is sharpened towards the front as indicated by reference numeral 16.1 and blunt towards the rear end as indicated by reference numeral 16.2, in order to ensure the formation of the arcuate incision and subsequent atraumatic stretching of the elastic blood vessel wall to receive the full circumference of the needle 14 or 16 and cannula 20.

Figure 2:
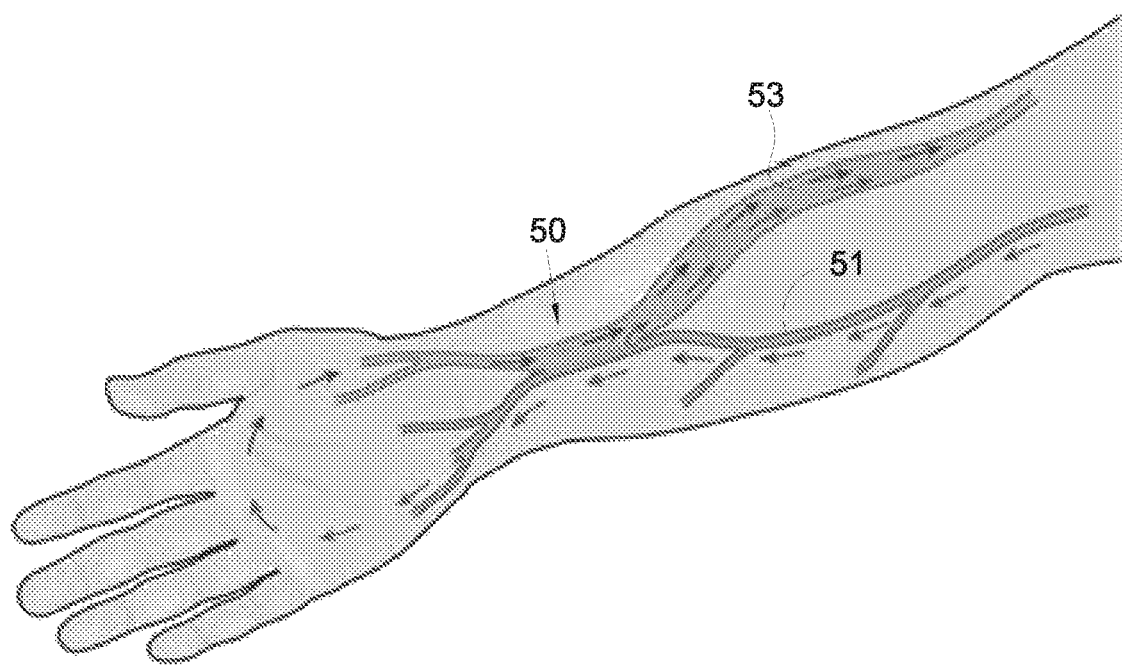
FIG. 2 shows a fistula which can be used during a dialysis treatment.

Prior to dialysis treatment, the fistula 50 is formed in a conventional fashion by connecting an artery 51 to a vein 53 as shown in FIG. 2. The increased blood flow and pressure through the vein 53 results in the thickening of the wall 54 as well as dilation of the vein to form the fistula 50.

Figure 7:
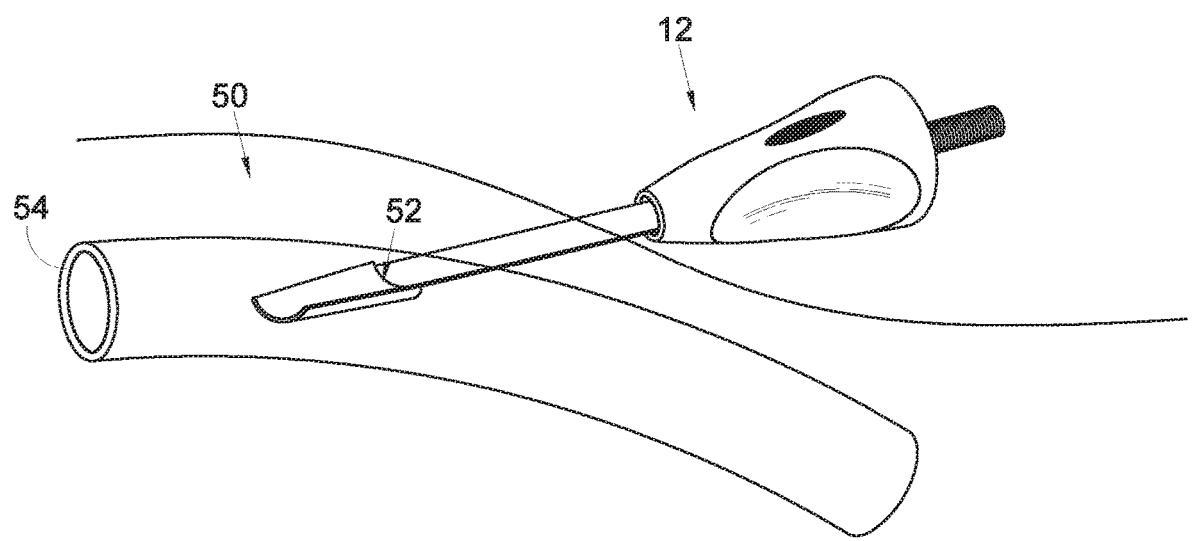
FIG. 7 shows a three-dimensional view of a cannula of the device of FIG. 3 inserted into a fistula.
Figure 8:
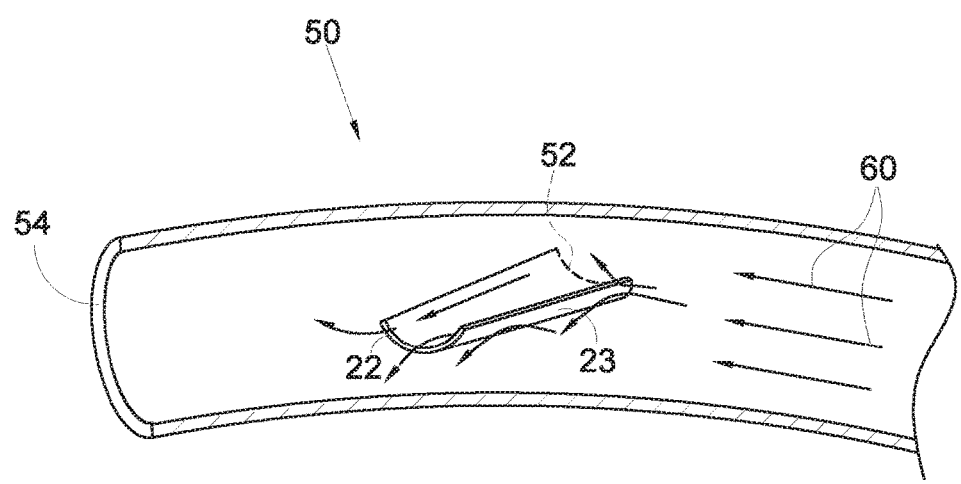
FIG. 8 shows, on an enlarged scale part of the cannula positioned in the fistula with the cannula in a closed condition.

Prior to the dialysis treatment, the needle 16 is inserted into the patient's body and through the wall 54 into the fistula 50. In doing so the incision 52 is formed, the incision 52 having an outer or convex side 56 and an inner or concave side 58. With the needle 16 in position, the distal end 22 of the cannula 20 is placed in the lumen of the fistula 50. Once the cannula 20 is in position, the needle 16 is removed leaving the cannula in position (FIGS. 7 and 8). In order to ensure correct orientation of the cannula, i.e. that the arcuate shape of the leading end portion is aligned with the arcuate incision 52, the needle 15 is provided with an orientation marking 41 corresponding to the marking 30.

Once in position, the cannula will typically be secured to the patient's body in a conventional fashion.

To facilitate the positioning of the cannula 20 in flow communication with the fistula or other blood vessel, the cannula may be pre-mounted on a placement needle. With specific reference to FIG. 25 of the drawings, a medical device 412, similar to that shown in FIG. 24 of the drawings, is mounted on a placement needle 300. In the embodiment shown, the placement needle 300 has a cutting end or tip similar to that of the needle 16 for the formation of an arcuate incision in a wall of the blood vessel in the manner described above. The placement needle 300 may also be used when replacing a medical device with a fresh medical device as described in more detail herebelow.

In view of the fact that the cannula 20, when in its rest or closed condition conforms substantially with the shape of the incision 52, the risk of blood escaping between the outer surface of the cannula 20 and the adjacent surface of the fistula 50 is reduced. Further, the distal end portion 23 of the cannula is in its normally closed condition which inhibits the entry of blood into the cannula through the distal end 22 thereof. As shown in FIG. 8 of the drawings, the distal end portion 23 of the cannula 20 enters the lumen of the fistula 50 at an angle such that it extends longitudinally within the lumen. The cannula 20 is typically orientated so that it extends in the direction of blood flow as indicted by arrows 60 which, together with the fact that the pressure within the fistula is higher than atmospheric pressure further assists in retaining the distal end portion 23 of the cannula 20 in its closed or rest condition.

Figure 11:
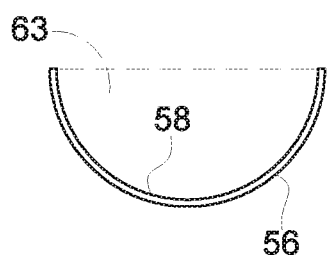
Figure 12:
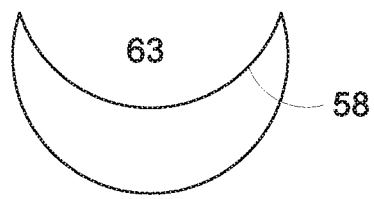
Figure 13:
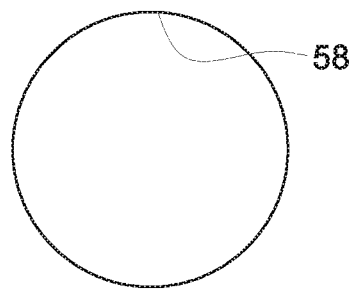

In order to connect the patient to a dialysis machine 62, the needle 14,414 is inserted into the cannula 20 from the proximal end 24 thereof. By displacing the needle longitudinally through the cannula, the rounded distal end 42 thereof urges the distal end portion 23 of the cannula away from its rest or closed condition toward an open condition. In this regard, it will be appreciated that as the leading or distal end of the needle 14,414 passes through the portion of the cannula 20 extending through the wall 54 of the fistula 50 it will displace the cannula away from its closed condition and in turn displace the portion of the wall 54 adjacent the inner side 58 of the incision 52 in the manner of a flap or curtain 63 as shown in FIGS. 11 to 13 of the drawings. The rounded end portion of the needle 14 ensures that the distal end portion 23 of the cannula is displaced from its rest condition without damaging the cannula or the wall of the fistula. Further, if desired, the distal end 42 of the needle 14,414 may be slightly bevelled to facilitate displacement of the portion of the wall 54 of the fistula 50 forming the flap or curtain 63. Once again, to ensure correct orientation of the needle 14,414, it is provided with an orientation marking 65. Once the needle 14,414 is in the desired position, it is secured to the cannula 20 using rotational male-female connectors.

Figure 19:
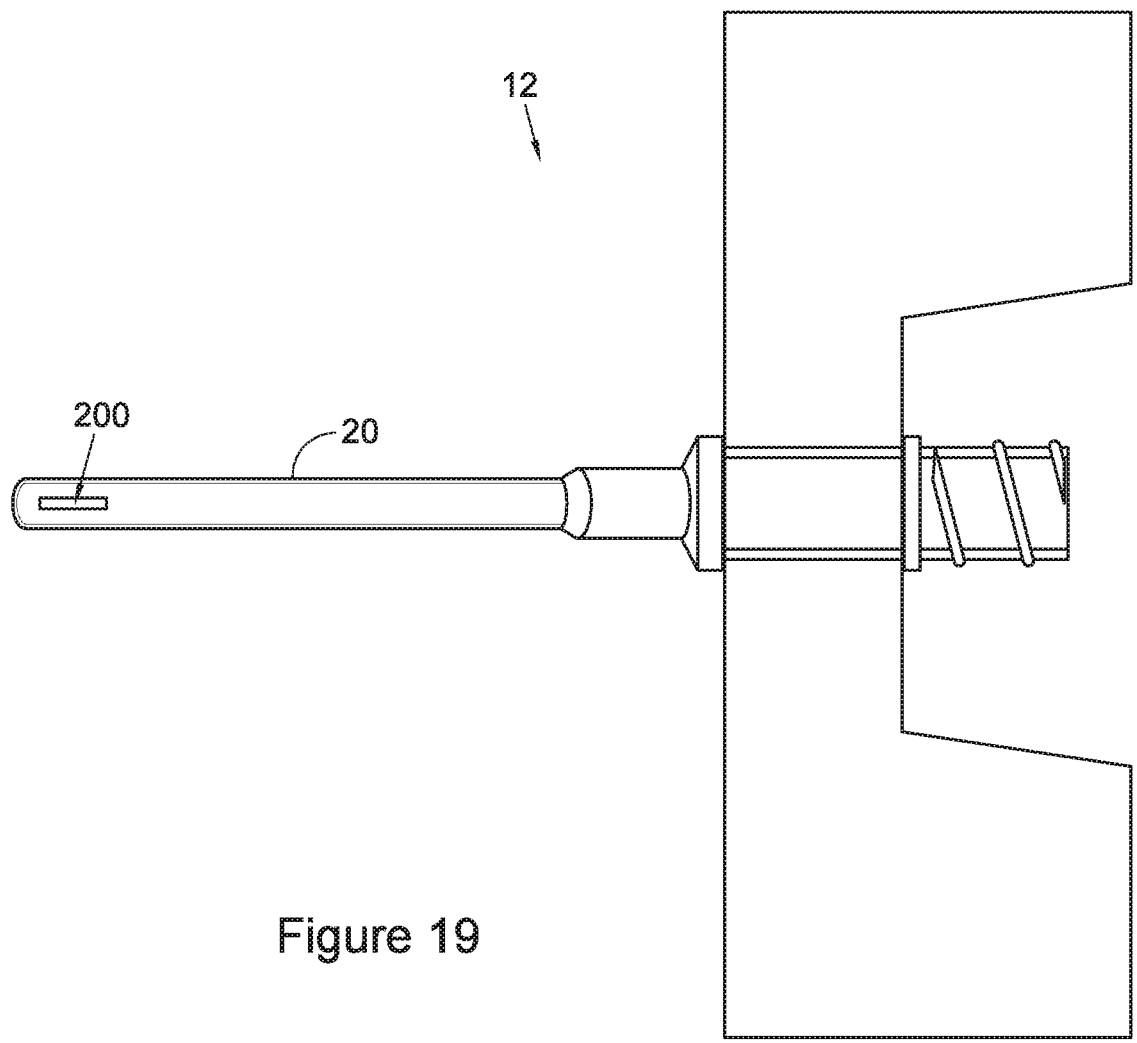
FIG. 19 shows another medical device in accordance with the invention.
Figure 20:
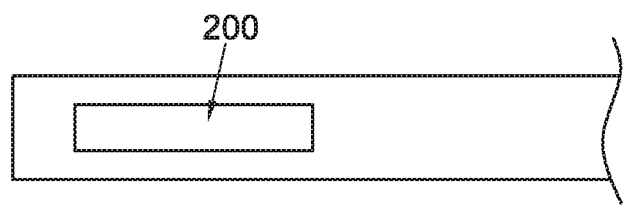
FIG. 20 shows, on an enlarged view, an end portion of the cannula forming part of the medical device of FIG. 19.
Figure 21:
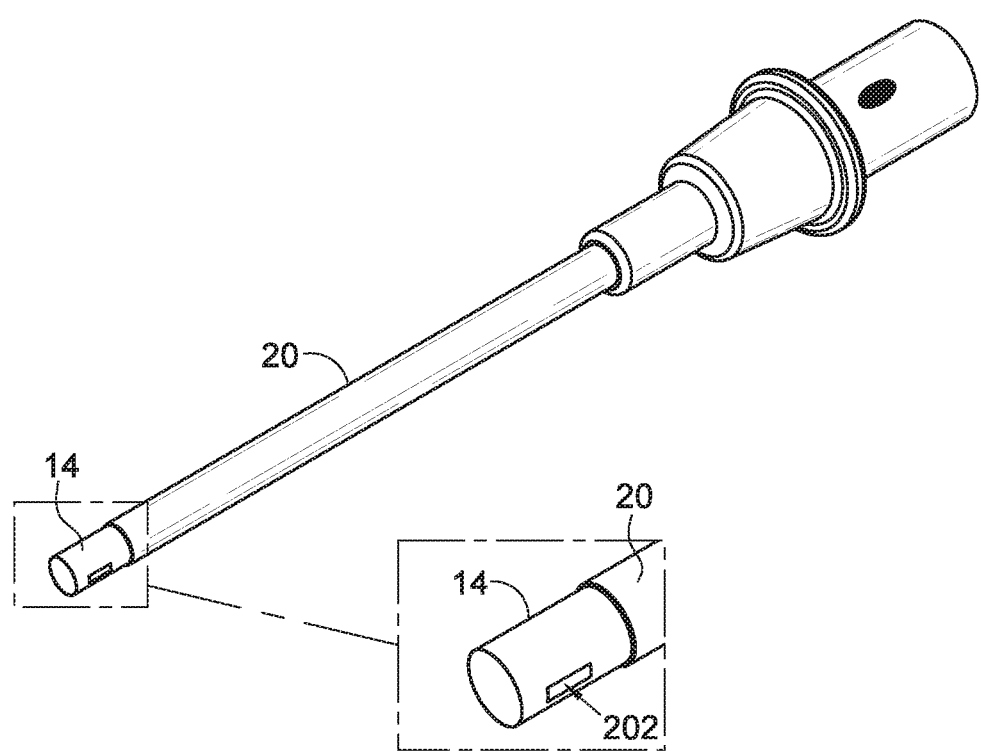
FIG. 21 shows a three-dimensional view of another dialysis needle inserted through a cannula in accordance with the invention.

The Inventor has found that the possibility exists that the distal end of the dialysis needle 14,414 may abut the sidewall of the blood vessel opposite to the incision 52. The sidewall may accordingly partially or fully obstruct the opening in the end of the needle 14,414 thereby inhibiting the flow of blood into or out of the needle. Accordingly, in another development of the invention, as illustrated in FIGS. 19 to 21 of the drawings, in which, unless otherwise indicated, the same reference numerals refer to the same parts referred to above, a transverse opening or eyelet 200 is provided in a side of the cannula 20 closely spaced from the distal end thereof. A similar transverse opening 202 is provided in a side of the dialysis needle 14,414 adjacent to the distal end thereof. As illustrated in FIG. 21 of the drawings, the end portion of the dialysis needle 14 in which the opening 202 is provided will protrude from the distal end of the cannula 20 in use. Should the distal end of the dialysis needle 14 abut against the sidewall of the fistula opposite to the incision 52, blood will still enter the dialysis needle 14 through the opening 202 thereby preventing a total blockage of the dialysis needle.

Figure 22:
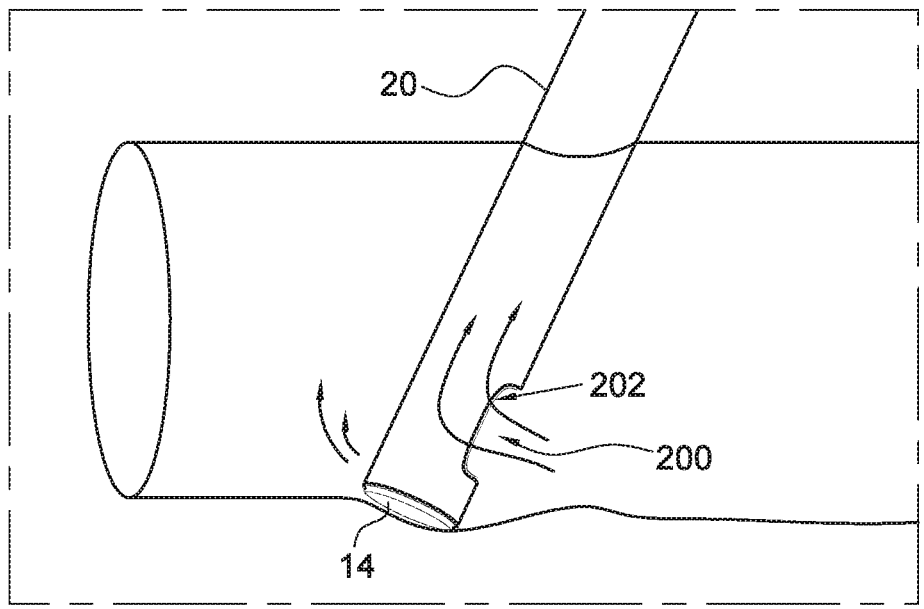
FIG. 22 shows an end portion of another dialysis needle in accordance with the invention with an end of the needle abutting against a sidewall of a blood vessel.
Figure 23:
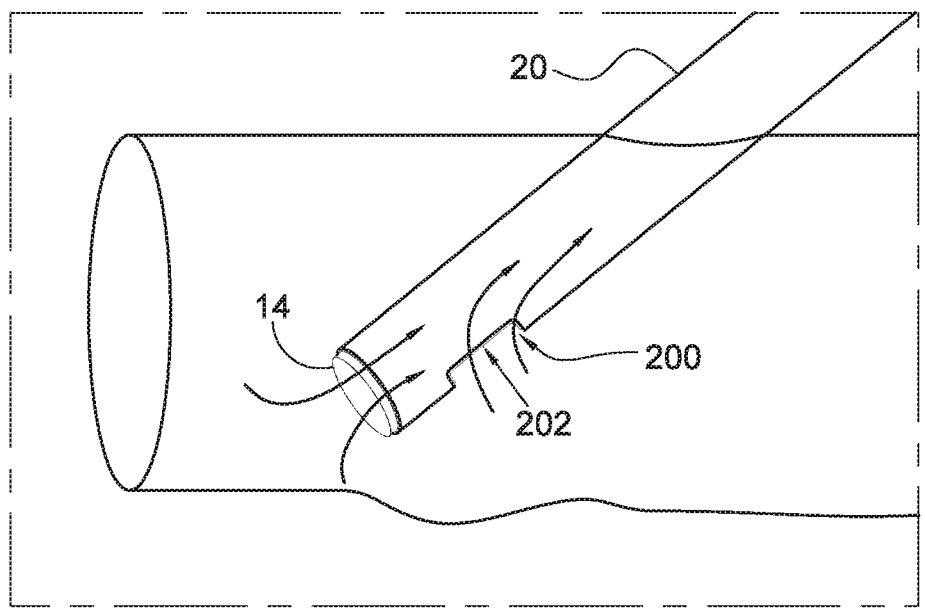
FIG. 23 shows a view similar to FIG. 28 with the end portion of the dialysis needle positioned correctly within a blood vessel.

In another embodiment of the invention, as illustrated in FIGS. 22 and 23, the lengths of the cannula 20 and dialysis needle 14 are selected such that when the dialysis needle 14 is inserted through the cannula 20, the distal ends of the needle and cannula are approximately coterminous. In this embodiment, the opening 200 in the cannula and the opening 202 in the dialysis needle 14 are in register. Accordingly, although the Inventor believes that this arrangement will reduce the risk of the distal ends of the cannula 20 and dialysis needle 14 coming into contact with the surface of the blood vessel opposite the incision, should this happen, blood will still flow through the openings 200, 202 thereby preventing a complete blockage of flow.

The proximal end of the needle 14,414 is connected by means of the pipe 48 in flow communication with the dialysis machine 62 such that when the distal end of the needle 14,414 extends into the lumen of the fistula 50 it is effectively connected in flow communication with the machine 62.

It will be appreciated that, for a dialysis treatment, two devices 12,412 will be inserted into the fistula at spaced-apart positions and will be connected, respectively, in flow communication with a suction or inlet side of the dialysis machine 62 and an outlet or discharge side of the dialysis machine 62 to form a closed loop to enable blood drawn from the fistula 50 to pass through the machine 62 and once treated to be returned to the fistula 50.

Once the dialysis treatment has been completed, the needle 14,414 can be withdrawn from the cannula 20. In so doing, as the distal end of the needle 14,414 is retracted, the distal end portion 23 of the cannula 20 will revert to its closed or rest condition inhibiting the flow of blood from the fistula through the cannula 20. Further, as the needle is withdrawn through the wall 54 of the fistula 50, the cannula returns to its closed condition and the portion of the wall 54 of the fistula 50 forming the flap 63 returns to the position where it abuts against the cannula thereby reducing the risk or extent of bleeding between the wall of the fistula 50 and the outer surface of the cannula 20.

Once the needle 14,414 has been completely withdrawn from the cannula 20, the cap 32 is mounted on the proximal end 24 of the cannula with the stylet 38 being received within the proximal end portion of the cannula in which it serves to displace any blood contained therein. Prior to mounting the cap 32 on the cannula, the cannula may be flushed, e.g. by injecting a heparin-saline solution under pressure through the cannula and into the fistula. Once the cap 32 is firmly in position, a sterile dressing will be applied over the head 18 and cap 32 positioned on top of the patient's skin.

During a subsequent dialysis treatment, the cap 32 is removed and a needle 14,414 inserted into the cannula in the manner described above. The provision of the stylet 38 minimises the amount of blood, if any, contained within the lumen of the cannula 20 which limits the small thrombi that may form in the lumen of the cannula 20 between dialysis treatments.

Between dialysis treatments, the patient may go home with the device 12, 412 in position as described above which then can be used at a subsequent dialysis treatment. The Inventor believes that the device 12, 412 will be capable of use for at least three dialysis treatments. In order to reduce the risk of infection, the Inventor believes that it will be appropriate to remove the device 12, 412 and insert or railroad a fresh device 12, 412 into position on a regular, e.g. weekly, basis. This can easily be performed by placing the long, hollow, round-tipped plastic needle or replacement rod 17 (FIG. 3) which is closed at one end into the fistula lumen through the cannula 20 of the device 12. While keeping the plastic needle 17 in place, the device 12, 412 can be withdrawn and a new one inserted, the plastic needle serving as a guide to align the distal end 22 of the cannula 20 of the fresh device 12, 412 with the incision 52 in the wall of the fistula. The orientation marking 30 enables the device 12, 412 to be correctly orientated relative to the incision 52.

In FIGS. 26 to 30 of the drawings, reference numeral 304 refers generally to a replacement rod in accordance with the invention. The replacement rod 304 includes a distal end 306 and a proximal end 308. The diameter of the replacement rod 304 extending longitudinally inwardly from the distal end 306 is greater than the diameter of the replacement rod 304 extending longitudinally inwardly from the proximal end 308 such that an angular shoulder 310 is defined at the intersection thereof. The shoulder 310 is inclined at an acute angle A relative to a longitudinal axis 312 of the replacement rod 304 and serves as an orientation means as described in more detail herebelow. Coloured dots 314, 316 are provided, respectively, adjacent to the distal and proximal ends 306, 308 and serve as orientation markings.

A blind bore extends longitudinally inwardly from the distal end 306.

The rod 304 is typically manufactured of a transparent, clear plastic polymer.

Figure 25:
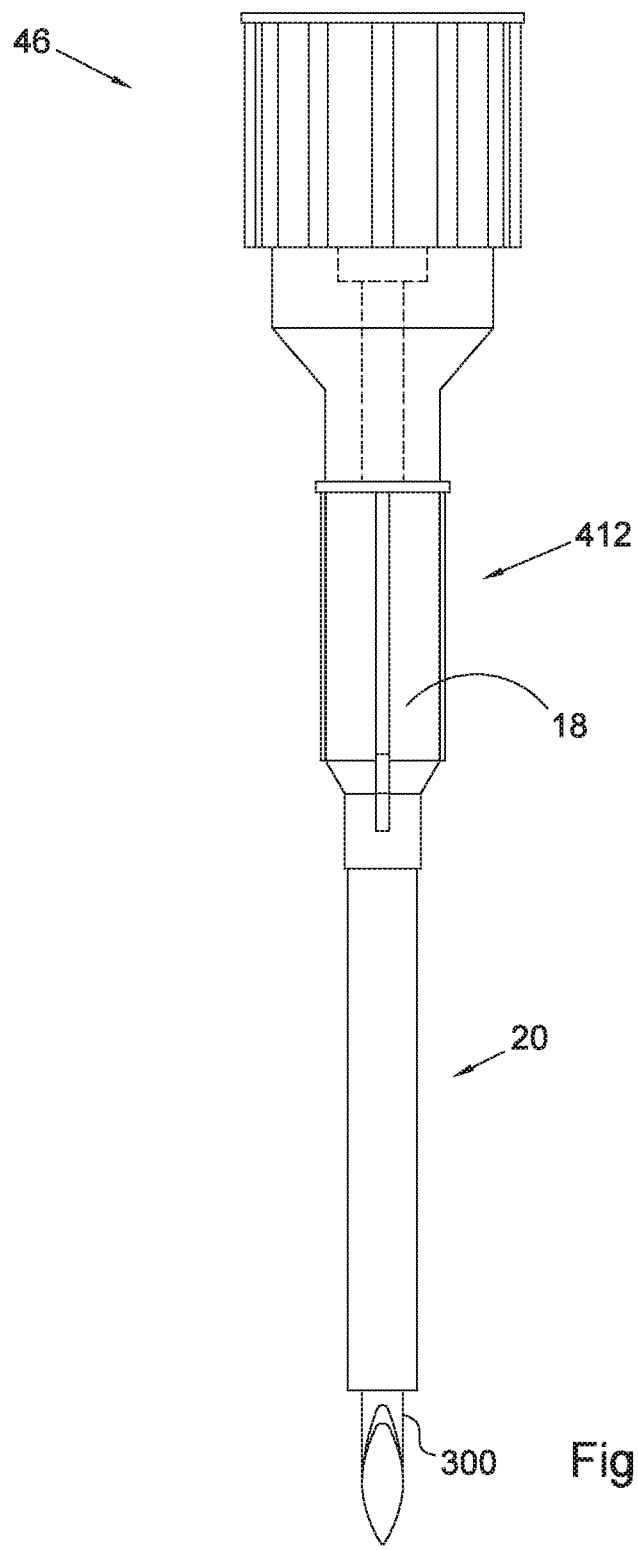
FIG. 25 shows the medical device of FIG. 24 mounted on a cutting tipped placement needle.
Figure 26:
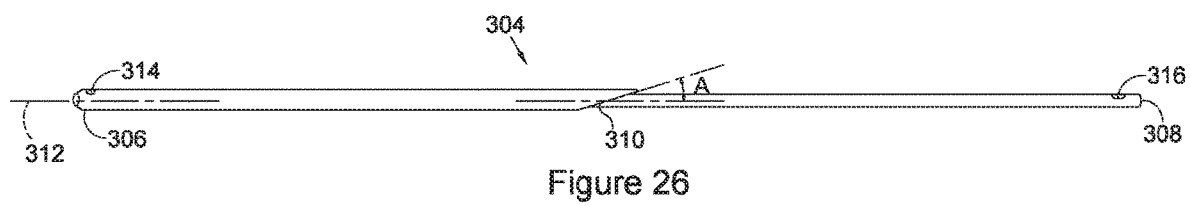
FIG. 26 shows a side view of a replacement rod in accordance with the invention.
Figure 27:
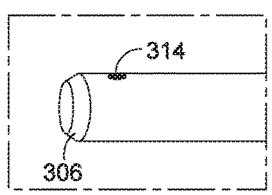
FIG. 27 shows a distal end portion of the replacement rod of FIG. 26.
Figure 28:
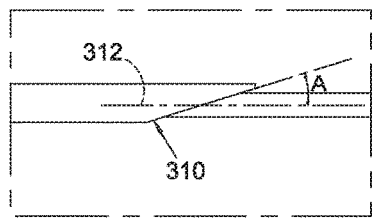
FIG. 28 shows an enlarged view of a middle portion of the replacement rod of FIG. 26.
Figure 29:
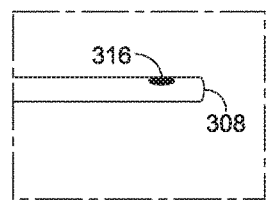
FIG. 29 shows a proximal end portion of the replacement rod of FIG. 26.
Figure 30:
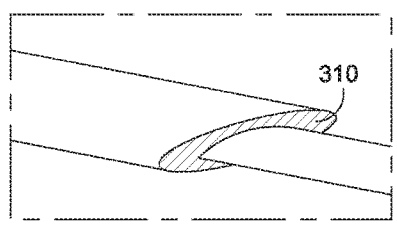
FIG. 30 shows an oblique view of the middle portion shown in FIG. 29.

The diameter of the distal end portion 306 of the replacement rod is selected such that it is snugly receivable in the cannula of the medical device with which the replacement rod 304 is intended to be used. The diameter of the proximal end portion of the replacement rod 304 is selected such that it is snugly receivable within a placement needle 300 on which a fresh medical device is mounted such as shown in FIG. 25.

Reference is now made to FIG. 31 to 38 of the drawings, in which the use of the replacement rod 304 in the replacement of an installed medical device with a fresh medical device 412 is described.

Figure 31:
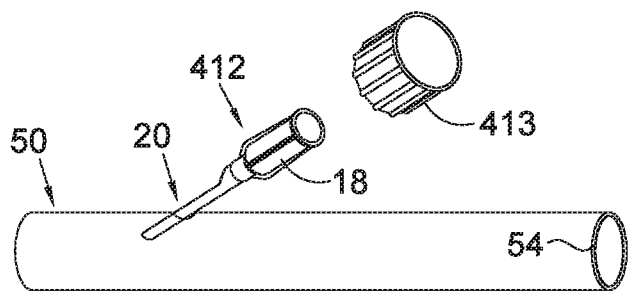
FIGS. 31 to 38 shows, sequentially, steps involved in the replacement of one medical device in accordance with the invention with a fresh medical device in accordance with the invention.

As illustrated in FIG. 31 of the drawings, the cap 413 is removed from the already installed medical device 412. The cannula 20 of the medical device 412 will be in its closed condition and accordingly no or little bleeding will occur.

Figure 32:
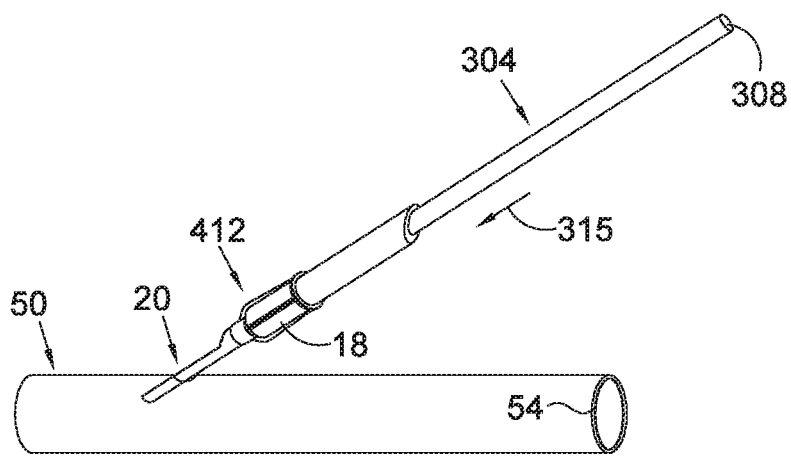
Figure 33:
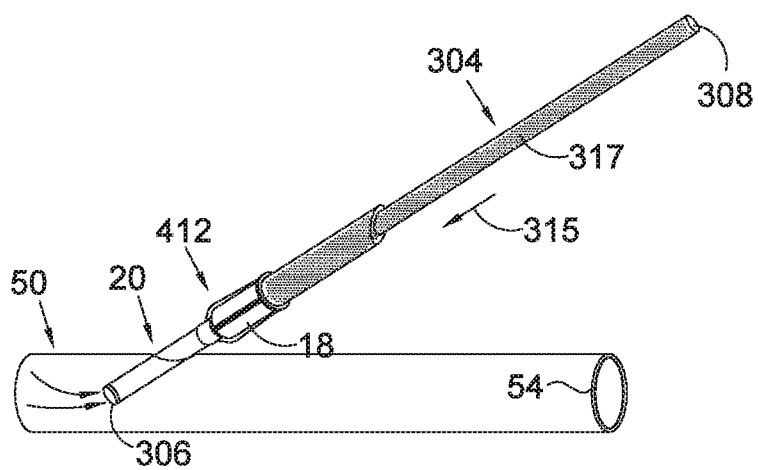
Figure 37:
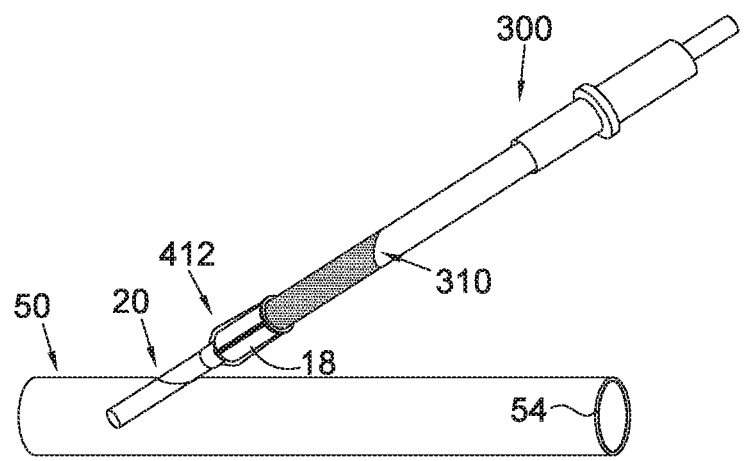
Figure 38:
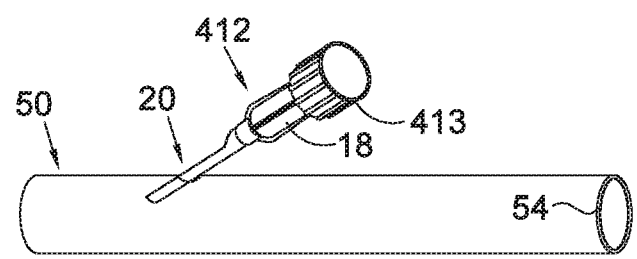

As illustrated in FIGS. 32 and 37 of the drawings, the distal end 306 of the replacement rod 304 is inserted into the medical device 412 and through the cannula 20 from the proximal end thereof in the direction of arrow 315. The rounded distal end 306 of the rod 304 urges the distal end portion 23 of the cannula 20 away from its rest or closed condition towards an open condition. When the distal end portion 306 of the replacement rod 304 enters the blood vessel 50, blood will enter the blind bore in the rod 304 and will be visible through the replacement rod 304 as illustrated by reference numeral 317 in FIG. 33. By making use of the dots 314, 316, the replacement rod 304 is positioned such that the orientation of the shoulder 310 is in a desired position to orientate a fresh device 412 relative to the incision or puncture site in the blood vessel as described below.

Figure 34:
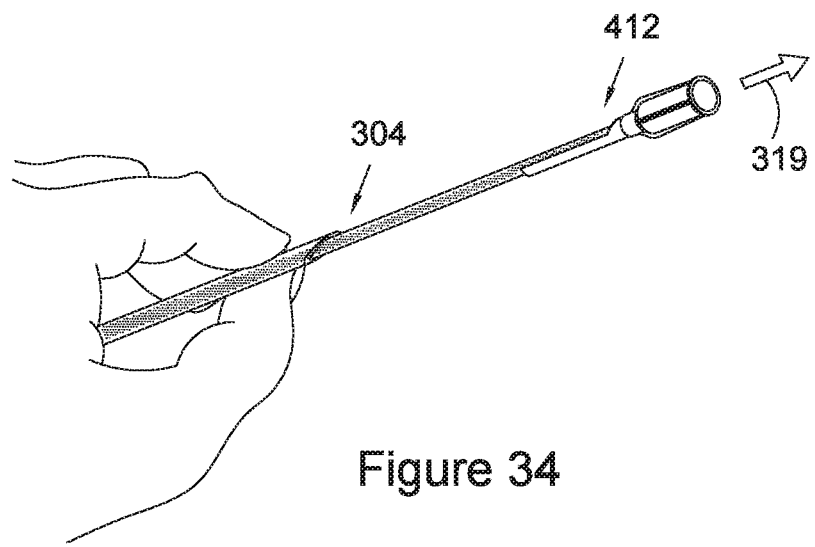

The replacement rod 304 is held in position with its distal end positioned in the blood vessel and the old medical device 412 is removed by sliding it longitudinally along the replacement rod 304 in the direction of arrow 319 as illustrated in FIG. 34 of the drawings.

Figure 35:
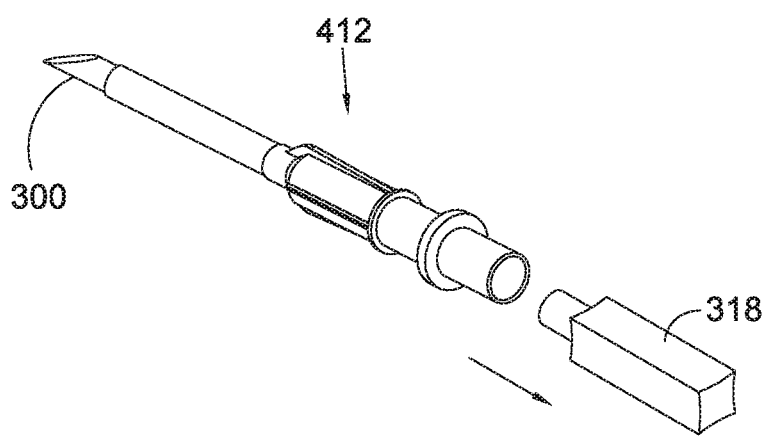

As illustrated in FIG. 35, a blocking cap 318 is removed from the placement needle 300 described above with reference to FIG. 25 of the drawings. A fresh medical device 412 is mounted or on the placement needle 300. Alternatively, the placement needle can be supplied with the medical device 412 already mounted thereon.

Figure 36:
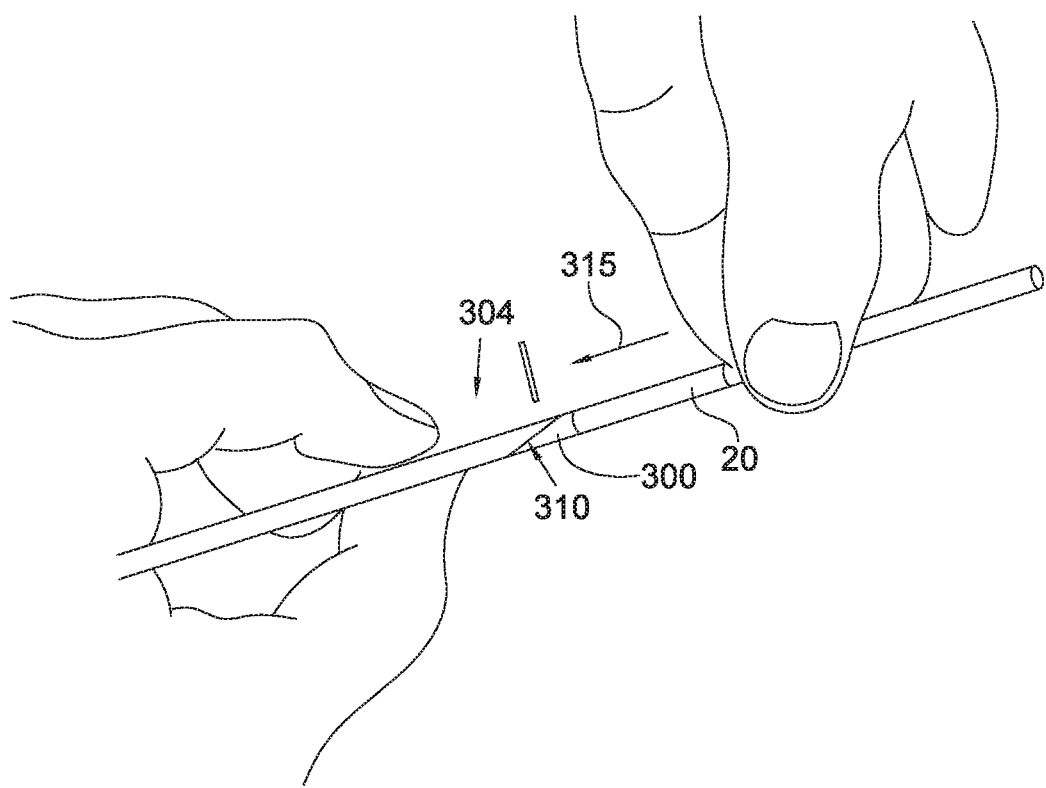

As illustrated in FIG. 36, the loaded placement needle 300, i.e. on which the fresh medical device 412 is mounted, is advanced over the proximal end 308 of the replacement rod 304, in the direction of arrow 315 until the leading or cutting end of the placement needle 300 abuts against the shoulder 310. The inclination of the shoulder 310 and the inclination of the leading end or cutting end of the placement needle 300 are complementary such that when they abut or marry up the fresh medical device 412 is automatically positioned in the correct orientation relative to the incision or puncture site in the blood vessel. In this regard, instead of a sharp tipped placement needle 300 use could be made of a blunt tipped needle. The shoulder 310 on the rod 304 will be selected to be complementary to and mate with the leading end of the needle to correctly orientate the needle as described above.

As illustrated in FIG. 37 of the drawings, the fresh medical device 412 is then displaced longitudinally along the placement needle 300 and the replacement rod 304 until the distal end thereof is positioned in the blood vessel.

Whilst retaining the fresh medical device 412 in position, the replacement rod 304 is removed and a cap 413 is positioned on the fresh medical device (FIG. 38) which, if desired, can be secured in position.

A major advantage with the invention is that it is not necessary to needle the fistula prior to each dialysis treatment. By leaving the cannula 20 in position, the same incision or puncture site can be used repeatedly. In this regard, the Inventor believes that the cannula 20 will probably be capable of use for at least three dialysis treatments. In addition, it may be possible to extend the use of an incision by periodically replacing the cannula with a fresh cannula in the manner described above. This in turn greatly extends the useful life of a fistula and reduces the frequency with which the patient has to endure the discomfort associated with the needling of the fistula. Another advantage with the invention is that when the device 12,412 is left in place, it has a low profile design, which prevents catching on clothes and linen. The Inventor further believes that patients will adopt the technology more easily in view of the fact that it is relatively inconspicuous. The Inventor further believes that, by virtue of the fact that the distal end portion 23 of the cannula 20, when in its rest condition, conforms largely to the crescent-shape of the incision 52, even if the device is inadvertently pulled out, it is expected that only minor bleeding would occur through the incision 52. Nevertheless, as a precaution, it may be advisable for a patient to wear an elasticated cover, e.g. in the form of a Velcro band or arm-stocking which covers both of the devices 12,412 and greatly reduces the risk of inadvertent withdrawal.

Although the invention has been described above with reference to a fistula, the Inventor believes that the invention will find application with other blood vessels including but not limited to an alternative method of performing central venous catheter haemodialysis. Accordingly, reference is now made to FIG. 14 of the drawings, in which, unless otherwise indicated, the same reference numerals used above are used to designate similar parts.

Figure 14:
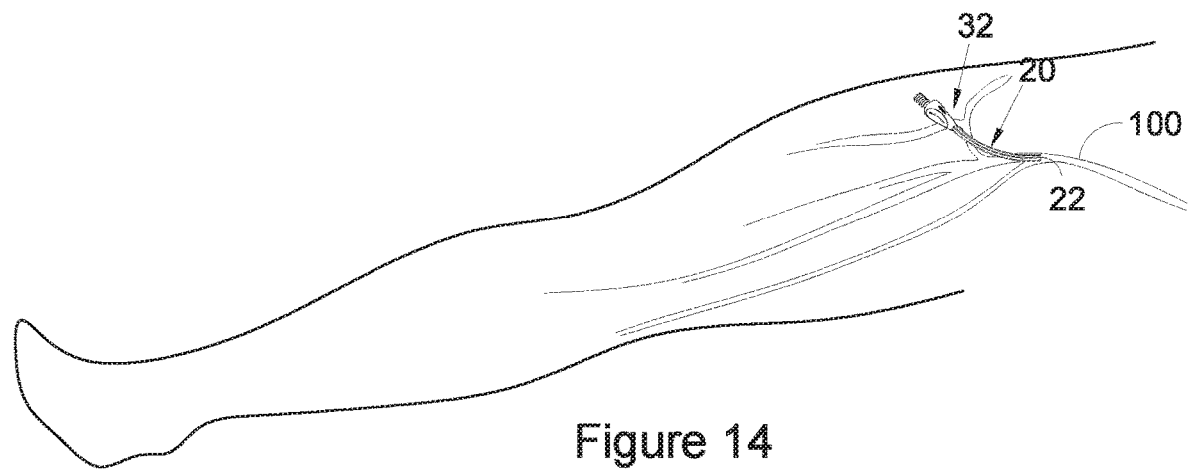
FIG. 14 shows a cannula of a device in accordance with the invention inserted into a femoral vein.

In FIG. 14 of the drawings, the cannula 20 is shown inserted into a common femoral vein 100.

The cannula 20 is typically inserted into the femoral vein 100 in the manner described above. Once inserted, the cannula 20 can be used in the manner described above with a single use HD-catheter being placed and removed by a trained nurse in a haemodialysis unit, under sterile conditions. The depth to which the catheter can be pushed in will be limited by the screw-on connectors.

Figure 15:
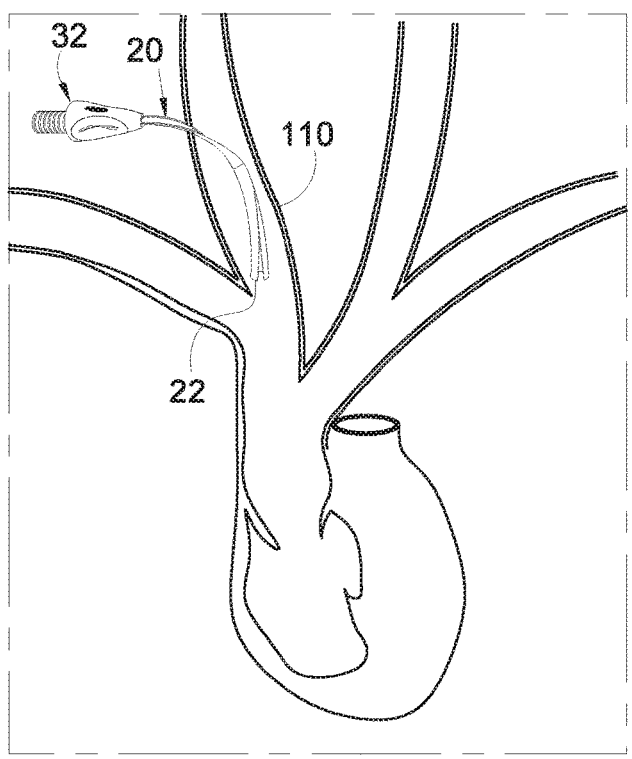
FIG. 15 shows a cannula in accordance with the invention inserted into an internal Jugular vein.

Reference is now made to FIG. 15 of the drawings, in which the cannula 20 is inserted into an internal jugular vein 110. Unless otherwise indicated, the same reference numeral as used above are used to designate similar elements and/or features.

Figure 16:
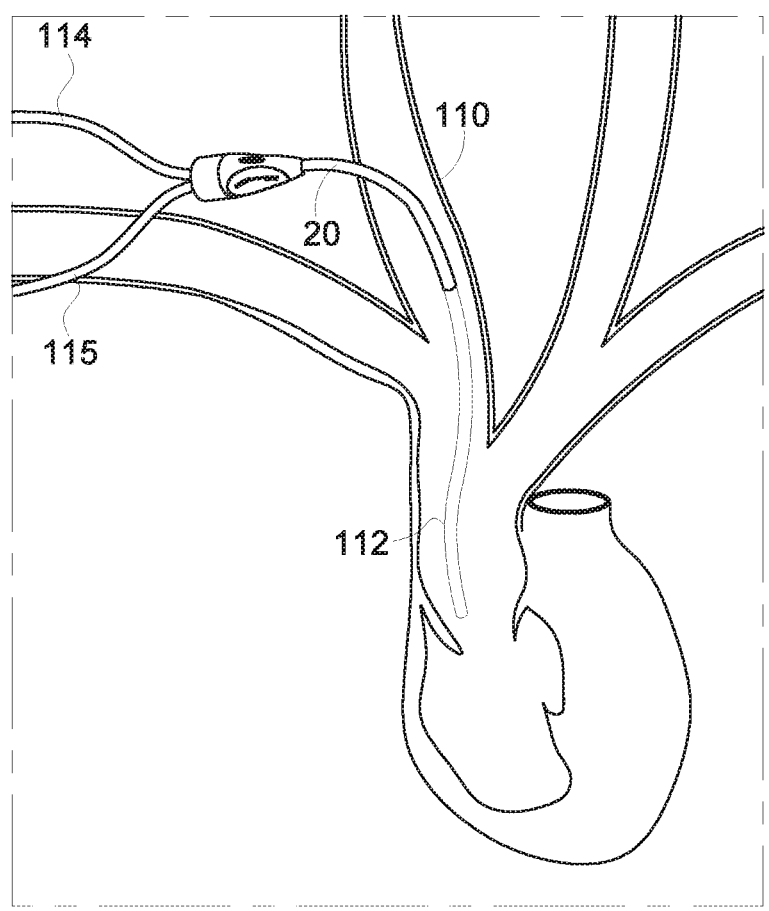
FIG. 16 shows the cannula of FIG. 15 with a central venous catheter in place.

As illustrated in FIG. 16 of the drawings, an HD-catheter 112 has two bores therethrough which are connected, respectively, by piping 114 and 115 to an inlet and outlet, respectively, of a dialysis machine.

The Inventor believes that the invention will increase the lifespan of a fistula by a factor of three or more. Consequently, secondary interventions to salvage ailing or blocked fistulas, which is very labour intensive and expensive, can be reduced or avoided.

A further advantage of the invention is that it permits easy and safe self-cannulation which will make home-dialysis a possibility. The Inventor believes that this will revolutionise current haemodialysis practice, saving enormous costs on in-unit dialysis and providing patents with the convenience and productivity benefits associated with home-based care. Currently, a patient on haemodialysis would typically spend 15 hours per week, during working hours, in a dialysis unit. With the present invention, a patient could have his cannula placed during a 30-minute appointment on a Monday and return to work thereafter. The patient could then dialyse in the evening at home thereby tremendously increasing productivity. The usual Wednesday and Friday sessions could be conducted entirely at home. Further, daily dialysis of shorter duration could be carried out without adversely affecting the effective life of the fistula. More frequent dialysis has been found to offer vastly superior health outcomes.

Further, patients will benefit from a reduced amount of painful sharp needling. This may further improve fistula lifespan as patients are often reluctant to be needled in "fresh" areas (as they should systematically utilise the entire fistula length).

Figure 39:
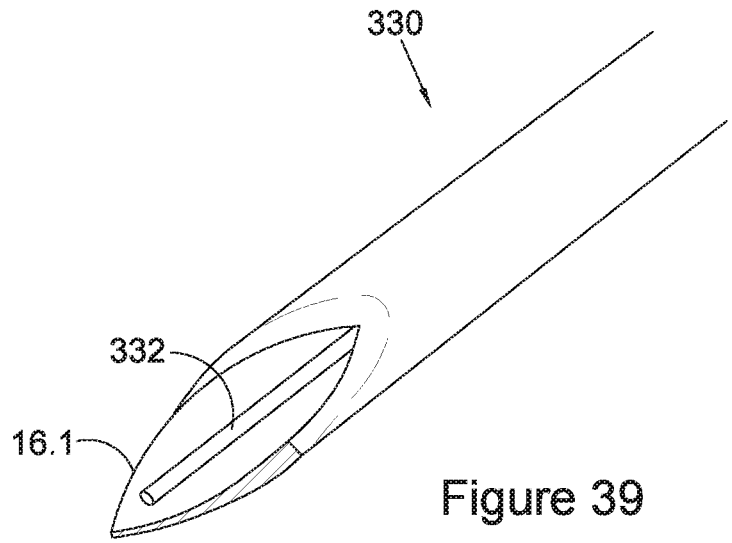
FIG. 39 shows a three-dimensional view of an end portion of another cutting tipped needle for use in the invention.
Figure 40:
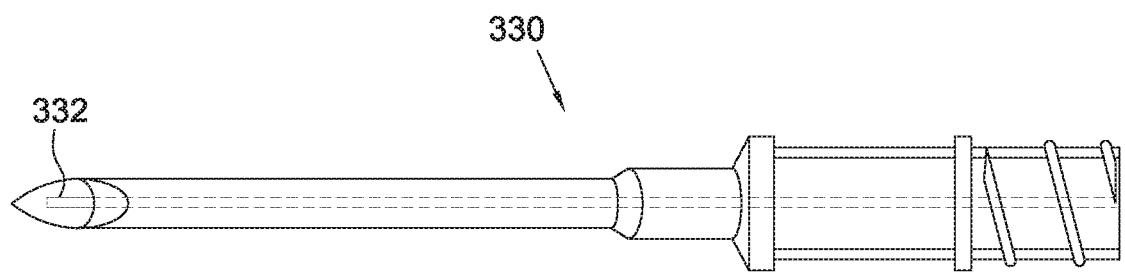
FIG. 40 shows a plan view of the needle of FIG. 39.
Figure 41:
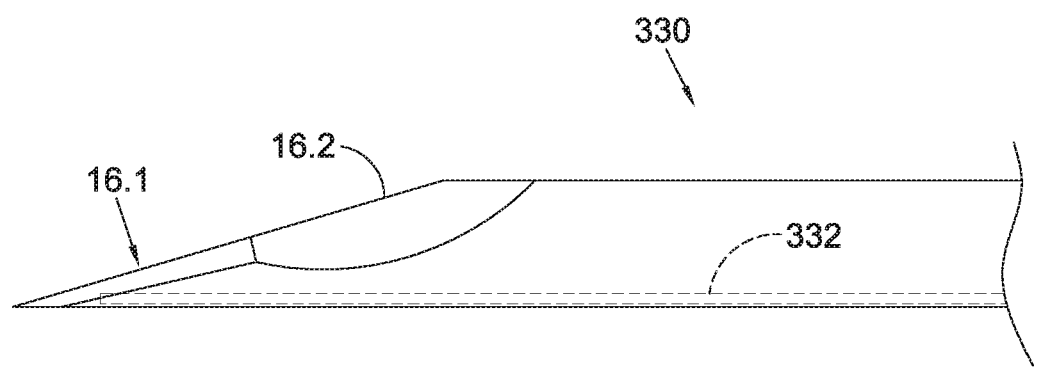
FIG. 41 shows a side view of an end portion of the needle of FIG. 39.
Figure 42:
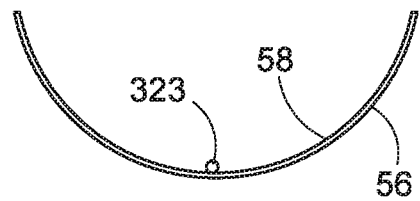
FIGS. 42 to 44 show the formation of a hole in a blood vessel making use of the cutting needle of FIG. 39.
Figure 43:
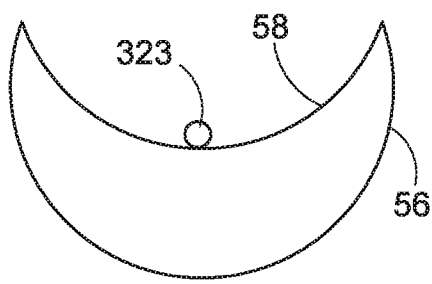
Figure 44:
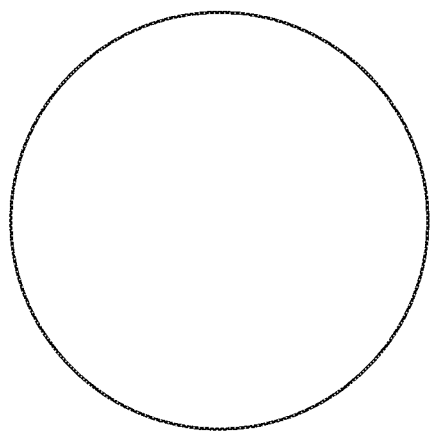

When accessing the arterial system of a patient, use is often made of a guidewire which is placed after ultrasound-guided puncture of the femoral artery with a thin needle. A sheath, having a substantially larger diameter, is then pushed into the artery using a simple dilator. This results in the formation of a relatively large generally circular hole in a wall of the of the femoral artery. By way of development and as described with reference to FIGS. 39 to 41 of the drawings, the invention provides a cutting tipped needle 330. The cutting tip needle 330 has a sharpened tip which is substantially identical to that of the needle 16,300 described above and the same reference numerals used above are used to designate similar parts. The main difference between the needle 330 and the placement needle 300 is that the needle 330 includes a guidewire engaging formation in the form of a small tube 332 which extends along the length of the bore of the cutting needle 330. Accordingly, as illustrated in FIGS. 42 to 48, the hole formed in a blood vessel by the needle 330 is similar to that described above with reference to FIGS. 10 to 13 with the exception of the formation of a notch 323 caused by the provision of the tube 332.

Figure 45:
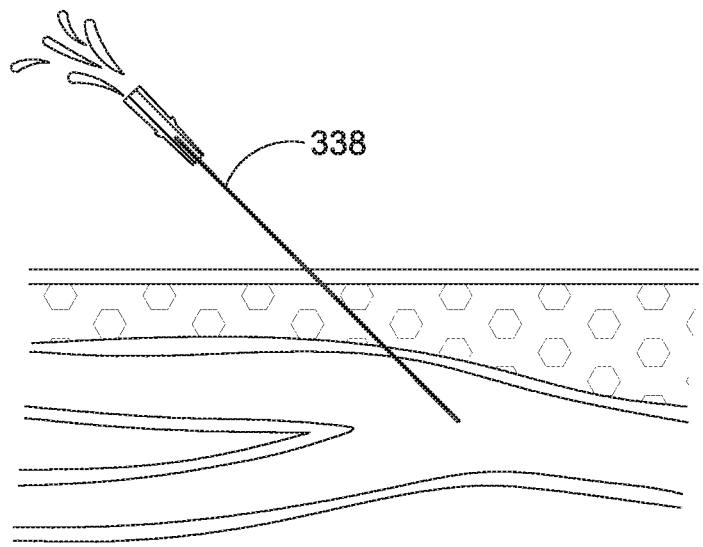
FIGS. 45 to 47 illustrate another method of accessing a blood vessel by inserting a medical device in accordance with the invention.
Figure 46:
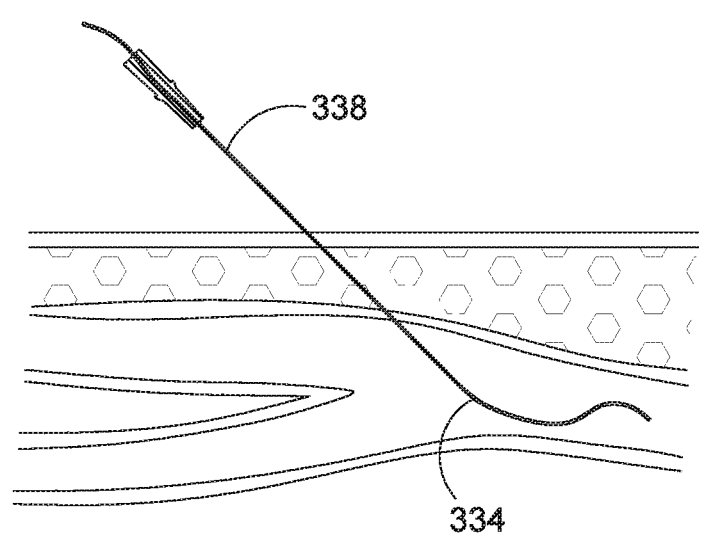
Figure 47:
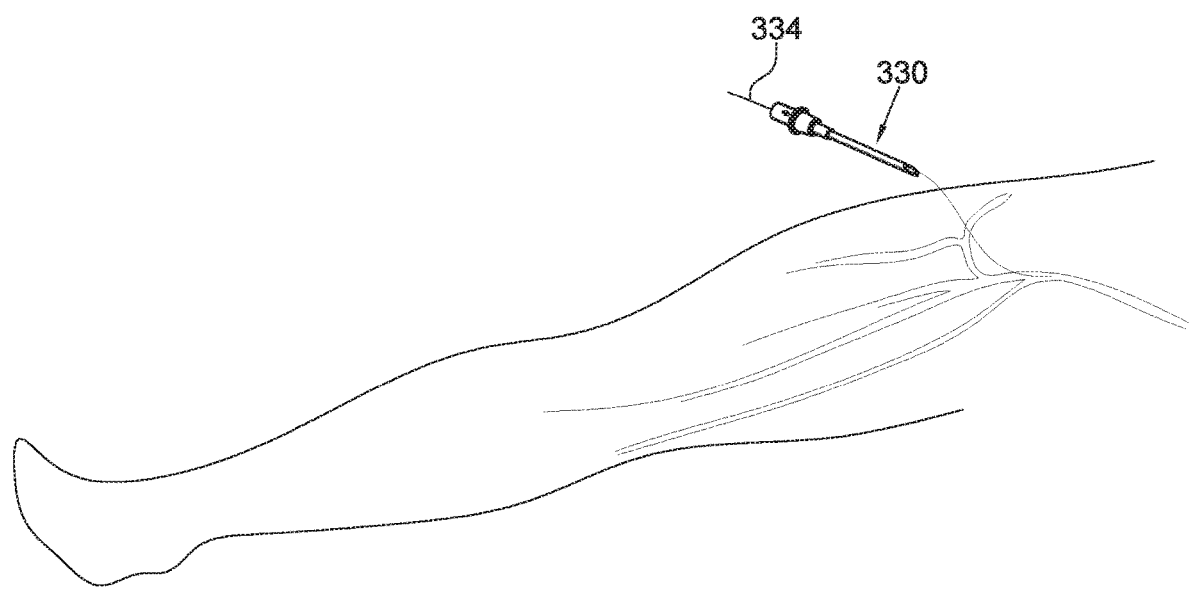
Figure 48:
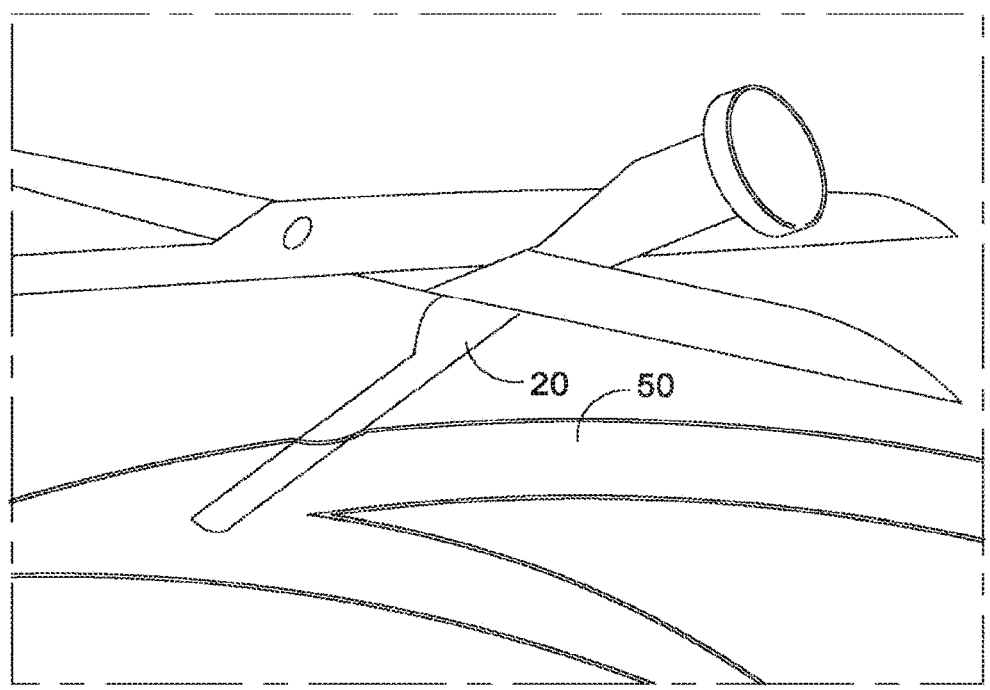
FIG. 48 illustrates an end portion of an installed medical device being cut and removed.

Hence, as illustrated in FIGS. 45 to 47 of the drawings, a guidewire 334 is positioned in a blood vessel 336 using a thin needle 338 in a conventional fashion. Once the guidewire 334 has been placed, the needle 338 is removed. An external portion of the guidewire 334 is then fed through the tube 332 as illustrated in FIG. 55. The cutting needle 330 is then displaced along the guidewire and into the blood vessel 336.

As described above, by virtue of the configuration of the end of the cutting needle 330 the incision will be generally arcuate in shape. A cannula which is preloaded on the cutting needle 330 can then be displaced from the needle into flow communication with the blood vessel in the manner described above. Once the cannula has been positioned, the cutting needle 330 can be removed.

The Inventor believes that the use of a cutting needle 330 and complementary cannula will avoid the formation of a large substantially circular hole in the blood vessel and thereby minimise the risk of bleeding from the puncture site. The Inventor believes that this aspect of the invention will find particular application when accessing a patient's femoral artery.

In one embodiment of the invention, at least that portion of the cannula which extends through the incision into the blood vessel may be formed of a bio-resorbable material. Accordingly, instead of removing the entire cannula when the procedure is completed, the portion of the cannula which is external to the blood vessel can be cut off, e.g. using a pair of scissors as illustrated in FIG. 50 of the drawings. The remaining portion of the cannula will form a haemostatic plug which further reduces the risk of bleeding from the site of the incision and obviates the need for the use of separate closure devices. It will be appreciated, however, that if desired, a dedicated closure device formed of a bio-resorbable material and having an arcuate cross-section may be inserted into the incision.

The invention claimed is:

1. A medical device which includes a cannula having a distal end portion which is insertable into a blood vessel, a proximal end, and a lumen extending through the cannula, in which the distal end portion of the cannula comprises a closure portion formed of a resiliently deformable material that extends longitudinally inwardly from the distal end portion of the cannula for at least part of a length of the cannula, in which the closure portion, is resiliently biased towards a closed configuration in which the closure portion inhibits fluid flow through the cannula, at least from the distal end portion to the proximal end, and which is displaceable against the bias away from the closed configuration of the closure portion to an open configuration by introduction of a needle through the lumen of the cannula and reverts the closure portion to the closed configuration when the needle is removed from the lumen of the cannula, in which the closure portion of the cannula has an arc shape in transverse cross-section when in the closed configuration.

2. The medical device as claimed in claim 1, in which the resiliently deformable material is a flexible polymeric material.

3. The medical device as claimed in claim 1, which includes a head to which the distal end portion of the cannula is connected and from which the head protrudes.

4. The medical device as claimed in claim 1, which includes a head to which the distal end portion of the cannula is connected and from which the head protrudes in which the head is formed of a rigid or semi-rigid material and is provided with gripping formations to facilitate manipulation of the medical device.

5. The medical device as claimed in claim 3 or claim 4, in which the head is coated with a soft material to improve patient comfort.

6. The medical device as claimed in claim 1, which includes a head to which the distal end portion of the cannula is connected and from which the head protrudes, in which the cannula includes a proximal end portion which protrudes from the head in a direction opposite to a direction in which the distal end portion protrudes and the proximal end portion is connected in flow communication with the distal end portion.

7. The medical device as claimed in claim 1, which includes a head to which the distal end portion of the cannula is connected and from which the head protrudes, in which the cannula includes a proximal end portion which protrudes from the head in a direction opposite to a direction in which the distal end portion protrudes and the proximal end portion is connected in flow communication with the distal end portion, in which the proximal end portion is rigid.

8. The medical device as claimed in claim 1, in which a transverse opening is provided in a side or wall of the cannula at a position closely spaced from the distal end portion thereof.

9. The medical device as claimed in claim 1, which includes a placement needle on which the cannula is mounted and relative to which the cannula is longitudinally displaceable to facilitate placement of the cannula.

10. The medical device as claimed in claim 1, which includes a placement needle on which the cannula is mounted and relative to which the cannula is longitudinally displaceable to facilitate placement of the cannula, and which includes a guide wire engagement arrangement configured to engage with a guide wire to facilitate correct placement of the placement needle and hence of the cannula.

11. The medical device as claimed in claim 1, wherein the closure portion of the cannula has a semi-circular arc shape in transverse cross-section when in the closed configuration.

12. A kit comprising (a) a cutting tipped needle for forming an arc shaped incision in a blood vessel and (b) a cannula having a distal end which is insertable into the blood vessel, a proximal end, and a lumen extending through the cannula, in which the distal end of the cannula comprises a closure portion formed of a resiliently deformable material that extends longitudinally inwardly from the distal end of the cannula for at least part of a length of the cannula, in which the closure portion, is resiliently biased towards a closed configuration in which the closure portion inhibits fluid flow through the cannula, at least from the distal end to the proximal end, and which is displaceable against the bias away from the closed configuration of the closure portion to an open configuration by introduction of a placement needle through the lumen of the cannula and reverts the closure portion to the closed configuration when the placement needle is removed from the lumen of the cannula, in which the closure portion of the cannula has an arc shape in transverse cross-section when in the closed configuration which is complementary in shape to the arc shaped incision formed by the cutting tipped needle to facilitate insertion of the distal end of the cannula into the blood vessel through the arc shaped incision, and in which the cannula is mountable on, and longitudinally displaceable relative to, the cutting tipped needle.

13. The kit of claim 12, including a second needle having a distal end and a proximal end, the distal end being shaped and dimensioned to be inserted through the lumen of the cannula into flow communication with the blood vessel into which the distal end of the cannula has been inserted.

14. The kit of claim 12, including a second needle having a distal end and a proximal end, the distal end being shaped and dimensioned to be inserted through the lumen of the cannula into flow communication with the blood vessel into which the distal end of the cannula has been inserted, in which the second needle is selected from:
 (a) a dialysis needle, the proximal end of the dialysis needle being connectable in flow communication with a dialysis machine;
 (b) a blunt-tipped atraumatic needle which is connected or connectable to a "Vacutainer" or other venepuncture system; and
 a syringe or a drip-IV-system into the blood vessel.

15. The kit of claim 12, wherein
 the cutting tipped needle is configured to form a semi-circular arc shaped incision in the blood vessel, and
 the closure portion of the cannula has a semi-circular arc shape in transfer cross-section when in the closed configuration which is complementary to the semi-circular arc shaped incision formed by the cutting tipped needle.

\* \* \* \* \*